(12) United States Patent
Matusik et al.

(10) Patent No.: US 11,389,604 B2
(45) Date of Patent: *Jul. 19, 2022

(54) GAS FLOW INDICATOR DEVICE

(71) Applicant: VPAS Group Pty Ltd, Malvern East (AU)

(72) Inventors: Matthew Matusik, Malvern East (AU); Mirko Tappero, Carrum Downs (AU)

(73) Assignee: VPAS Group Pty Ltd, Malvern East (AU)

( * ) Notice: Subject to any disclaimer, the term of this patent is extended or adjusted under 35 U.S.C. 154(b) by 458 days.

This patent is subject to a terminal disclaimer.

(21) Appl. No.: 16/627,289

(22) PCT Filed: Jun. 28, 2018

(86) PCT No.: PCT/AU2018/050665
§ 371 (c)(1),
(2) Date: Dec. 28, 2019

(87) PCT Pub. No.: WO2019/000043
PCT Pub. Date: Jan. 3, 2019

(65) Prior Publication Data
US 2020/0129713 A1    Apr. 30, 2020

(30) Foreign Application Priority Data

Jun. 28, 2017    (AU) ................................ 2017902508

(51) Int. Cl.
*A61M 16/00* (2006.01)
*A61M 16/06* (2006.01)
*A61M 16/08* (2006.01)

(52) U.S. Cl.
CPC ........ *A61M 16/0003* (2014.02); *A61M 16/06* (2013.01); *A61M 16/0816* (2013.01);
(Continued)

(58) Field of Classification Search
CPC .............. A61M 16/0003; A61M 16/06; A61M 16/0816; A61M 2016/003;
(Continued)

(56) References Cited

U.S. PATENT DOCUMENTS

| 828,108 A | 8/1906 | Graham |
| 2,389,282 A | 11/1945 | Stegeman |
(Continued)

FOREIGN PATENT DOCUMENTS

| DE | 1176885 B | 8/1964 |
| GB | 1396759 A | 6/1975 |
(Continued)

*Primary Examiner* — Samchuan C Yao
*Assistant Examiner* — Sarah B Lederer
(74) *Attorney, Agent, or Firm* — Forge IP, PLLC

(57) ABSTRACT

A gas flow indicator device has a housing defining a chamber. An annular indicator extends over the chamber enabling gas to enter along a bore and is spaced from an inner surface, defining an annular space. A moveable concealment member has an annular skirt receivable into the annular space so one end provides a seal against an annular surface at an end wall while a transverse wall at the other end defines an opening providing resistance to gas flow. The skirt can be held in sealing engagement at the annular surface to conceal the indicator through a window. Increasing gas flow rate overcomes the bias of a biasing member and moves the concealment member to expose the indicator and provide a visual indication of gas flow. A fitting member has an engagement portion operable to constrain the biasing member to preclude vibrations and/or prevent its full compression.

32 Claims, 16 Drawing Sheets

(52) U.S. Cl.
CPC ... *A61M 16/0683* (2013.01); *A61M 2016/003* (2013.01); *A61M 2205/583* (2013.01)

(58) Field of Classification Search
CPC ........ A61M 16/0075; A61M 2205/583; A61M 16/20; G01F 1/10; F23D 14/82
See application file for complete search history.

(56) References Cited

U.S. PATENT DOCUMENTS

| | | | |
|---|---|---|---|
| 2,662,502 A | 12/1953 | Turner | |
| 2,843,121 A | 7/1958 | Hudson | |
| 3,119,369 A | 1/1964 | Harland et al. | |
| 3,256,876 A | 6/1966 | Elam | |
| 3,408,865 A | 11/1968 | Chenault | |
| 3,650,599 A | 3/1972 | Pedersen | |
| 3,890,967 A | 6/1975 | Elam et al. | |
| 4,064,751 A | 12/1977 | Deisenroth et al. | |
| 4,098,271 A | 7/1978 | Maddock | |
| D256,000 S | 7/1980 | Molijn | |
| D266,316 S | 9/1982 | Du Vall | |
| 4,745,877 A | 5/1988 | Chang | |
| 4,938,078 A | 7/1990 | Kobold | |
| 4,945,918 A | 8/1990 | Abernathy | |
| 5,038,773 A | 8/1991 | Norlien et al. | |
| 5,337,617 A | 8/1994 | Dimeff | |
| 5,343,859 A | 9/1994 | Kikut | |
| 5,606,131 A | 2/1997 | Pope | |
| 5,845,597 A | 12/1998 | Karpal | |
| 5,857,460 A | 1/1999 | Popitz | |
| 5,911,219 A | 6/1999 | Alysworth et al. | |
| 6,338,279 B1 | 1/2002 | Tsataros | |
| 6,386,196 B1 | 5/2002 | Culton | |
| 7,004,168 B2 | 2/2006 | Mace et al. | |
| 7,013,726 B1 | 3/2006 | Drummond et al. | |
| 7,040,319 B1 | 5/2006 | Kelly et al. | |
| 7,055,520 B2 | 6/2006 | Swisa | |
| 7,159,533 B1 | 1/2007 | Redd et al. | |
| D551,999 S | 10/2007 | Makkonen et al. | |
| 7,730,847 B1 | 6/2010 | Redd et al. | |
| 7,891,311 B2 | 2/2011 | Logan et al. | |
| D657,399 S | 4/2012 | Memoto | |
| 10,307,558 B2 | 6/2019 | Matusik | |
| 10,314,998 B2 | 6/2019 | Zhan et al. | |
| 2005/0205098 A1 | 9/2005 | Lampotang et al. | |
| 2006/0070458 A1 | 4/2006 | Jones et al. | |
| 2006/0130838 A1 | 6/2006 | Lee et al. | |
| 2006/0266133 A1 | 11/2006 | Kim et al. | |
| 2007/0221223 A1* | 9/2007 | McDermott | A61M 16/08 128/204.22 |
| 2009/0114225 A1 | 5/2009 | Tappehorn et al. | |
| 2009/0145349 A1 | 6/2009 | Herbert | |
| 2009/0165801 A1 | 7/2009 | Ostrowski | |
| 2009/0301474 A1 | 12/2009 | Korneff et al. | |
| 2010/0282253 A1* | 11/2010 | Newman, Jr. | A61M 16/208 128/205.24 |
| 2012/0048274 A1 | 3/2012 | Bayron et al. | |
| 2012/0055471 A1 | 3/2012 | Hadas et al. | |
| 2012/0298109 A1 | 11/2012 | Phifer et al. | |
| 2012/0325215 A1 | 12/2012 | Levenick et al. | |
| 2015/0196723 A1 | 7/2015 | Matusik | |
| 2016/0135899 A1 | 5/2016 | Limon | |
| 2019/0269875 A1 | 9/2019 | Matusik | |

FOREIGN PATENT DOCUMENTS

| | | |
|---|---|---|
| GB | 2073893 A | 10/1981 |
| JP | 2016017756 A | 2/2016 |
| WO | 2014026221 A1 | 2/2014 |

\* cited by examiner

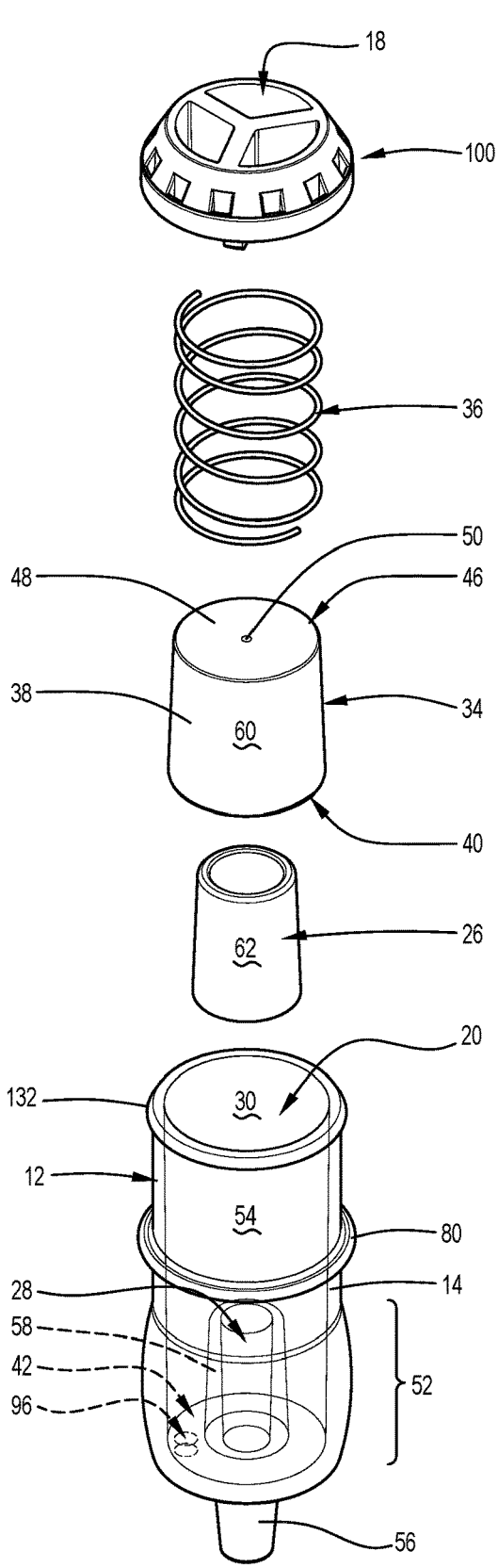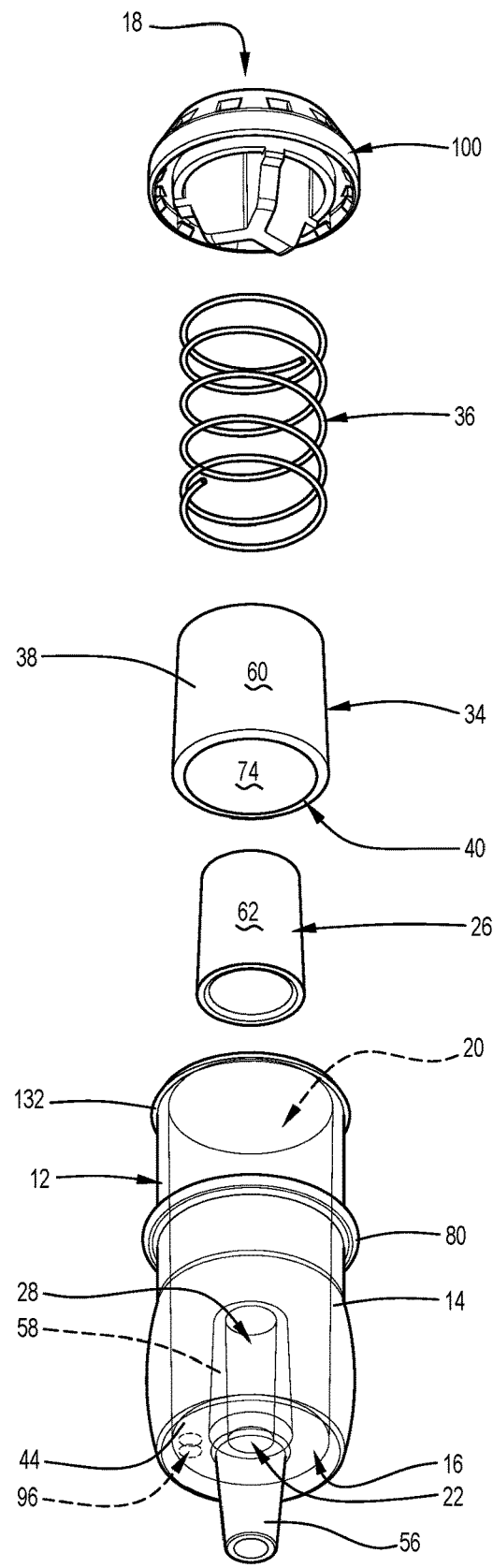

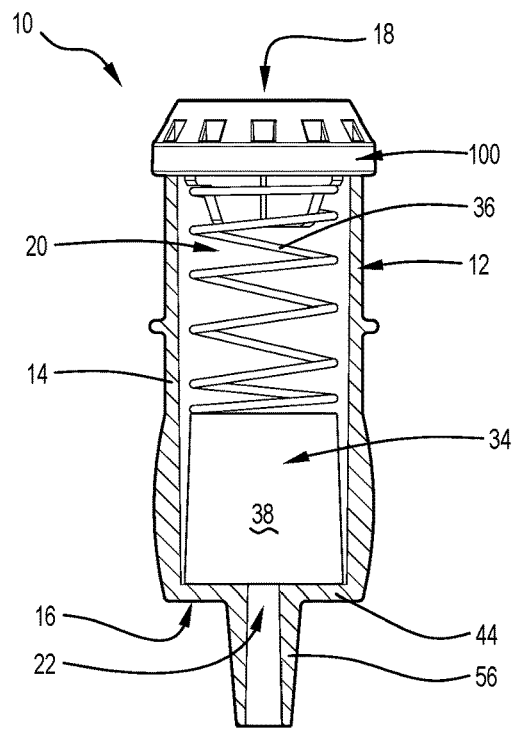 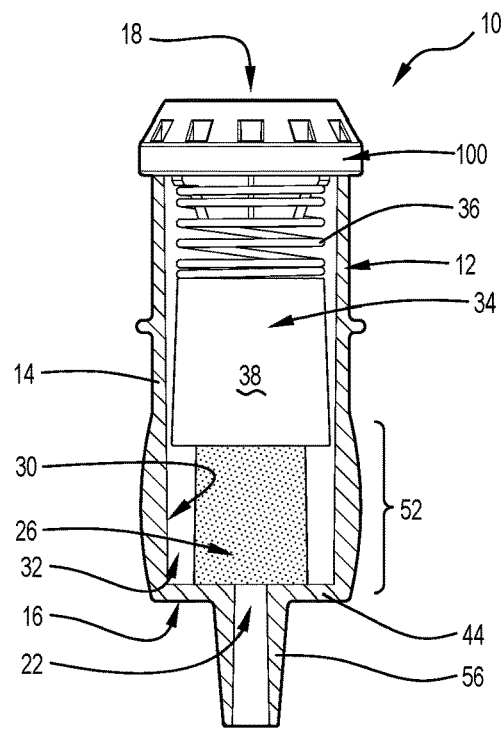
FIG. 14  FIG. 15
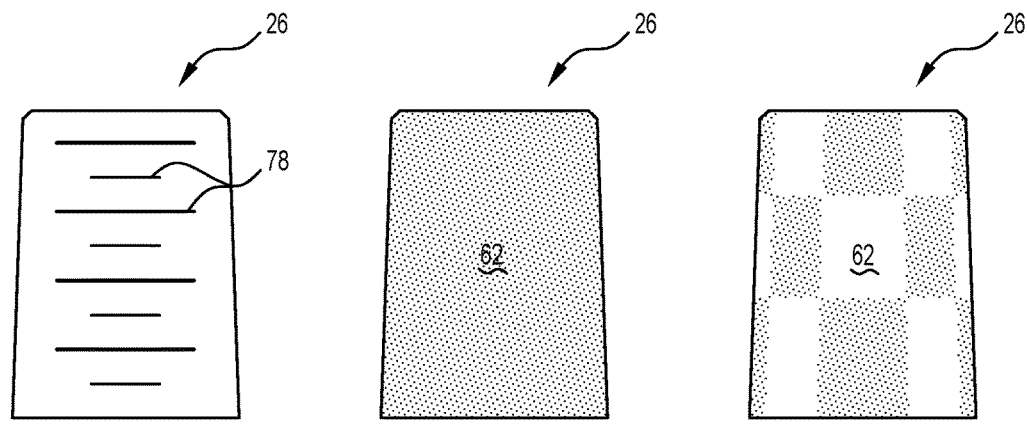
FIG. 16  FIG. 17  FIG. 18

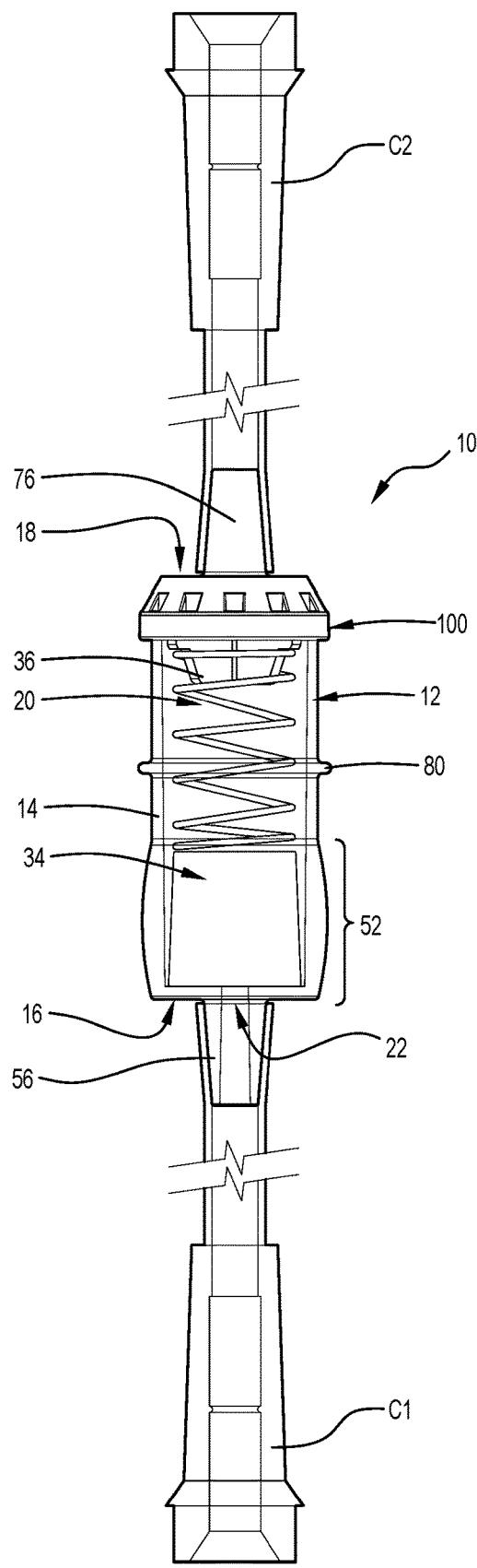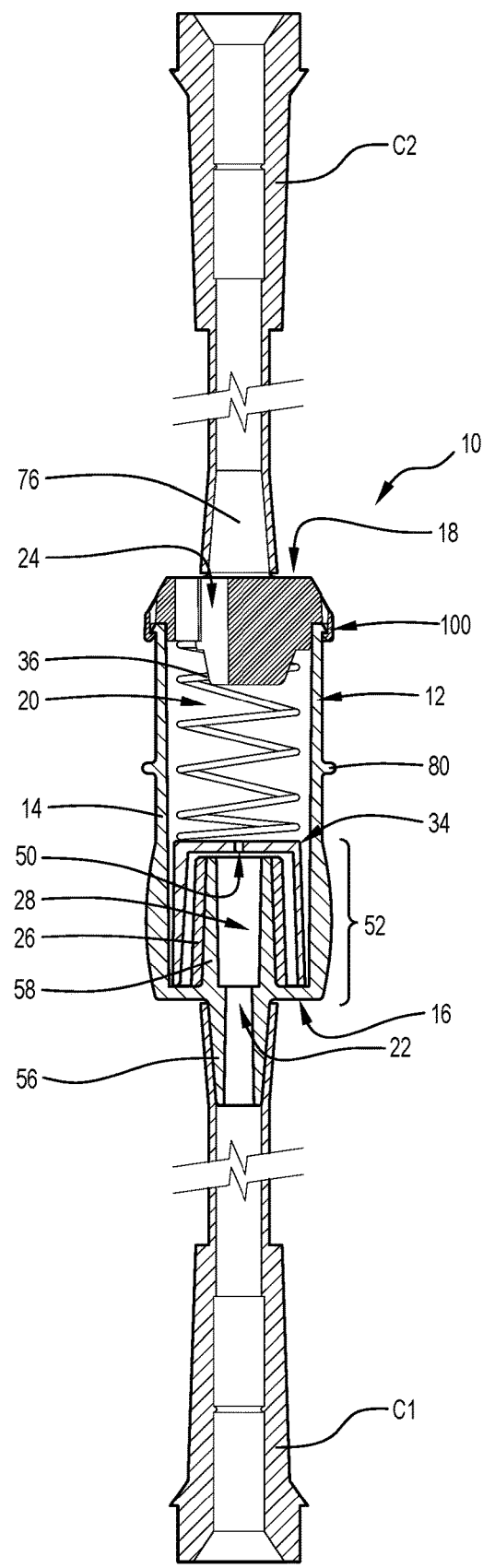
*FIG. 19*  *FIG. 20*

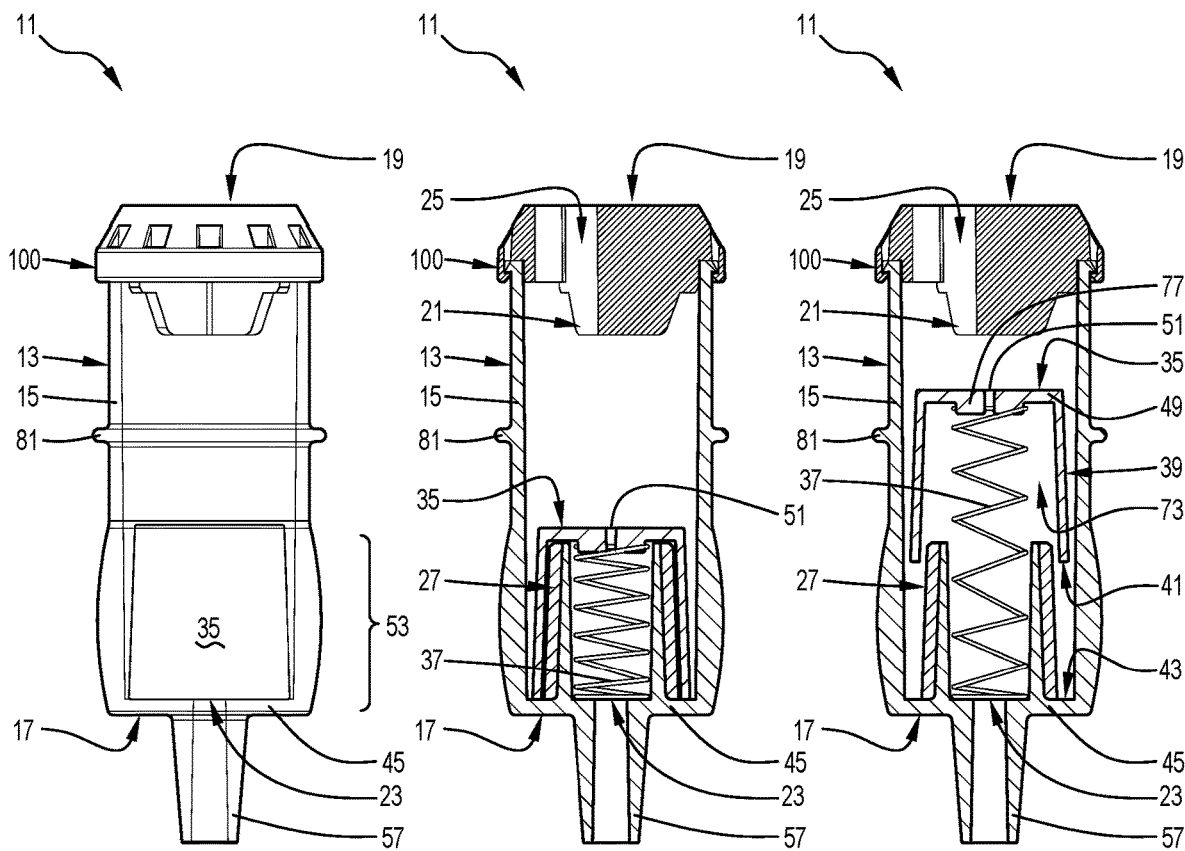
FIG. 21  FIG. 22  FIG. 23
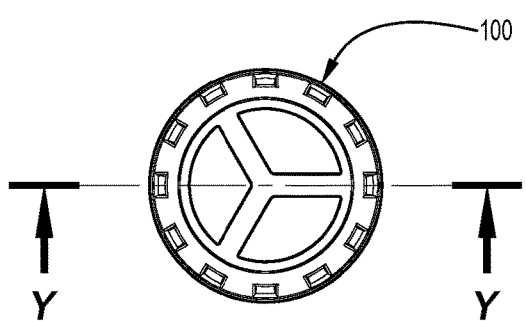
FIG. 24

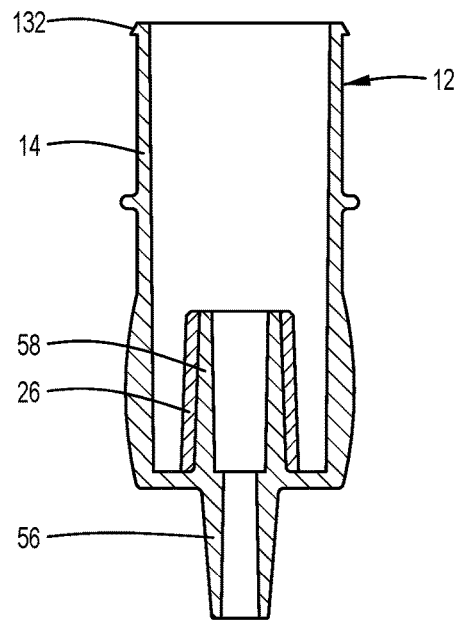
FIG. 29
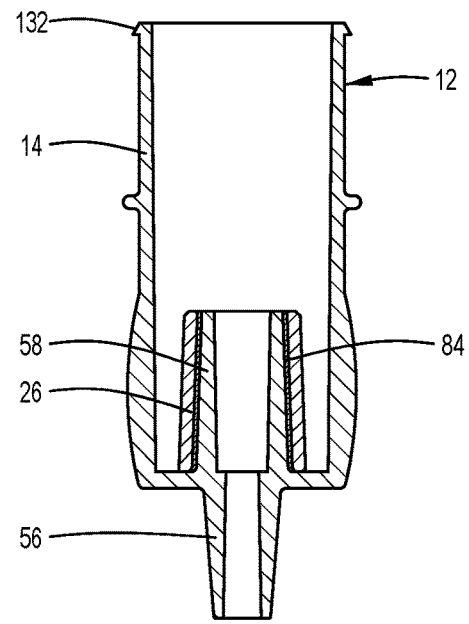
FIG. 30
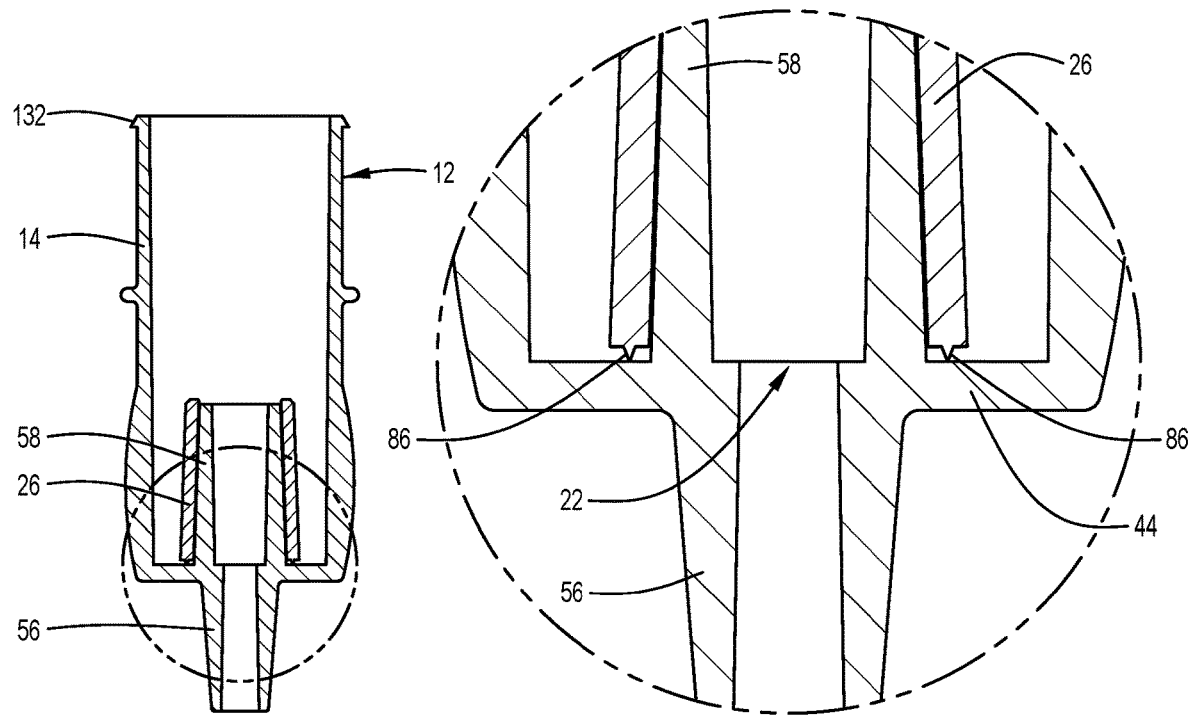
FIG. 31  FIG. 32

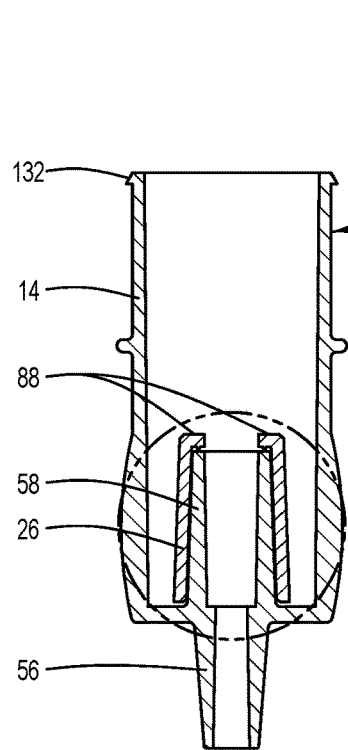
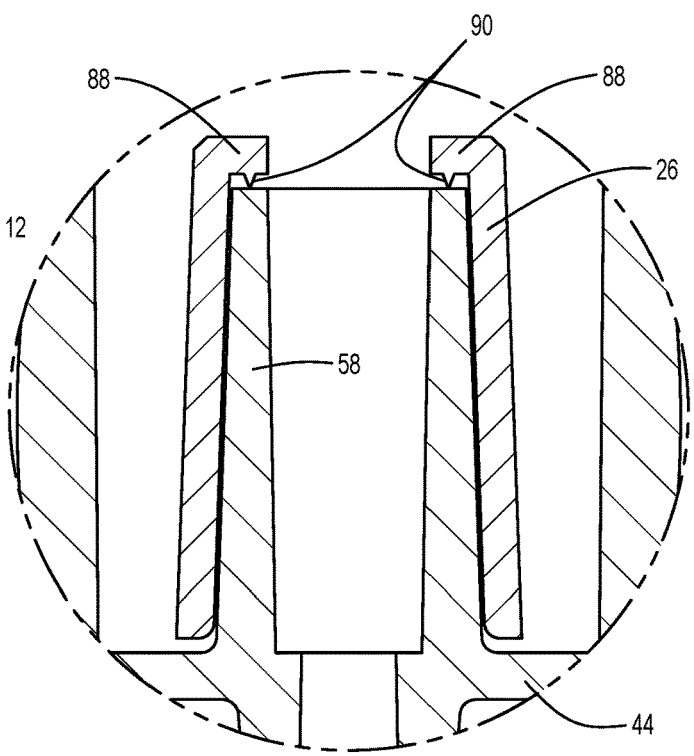
FIG. 33  FIG. 34
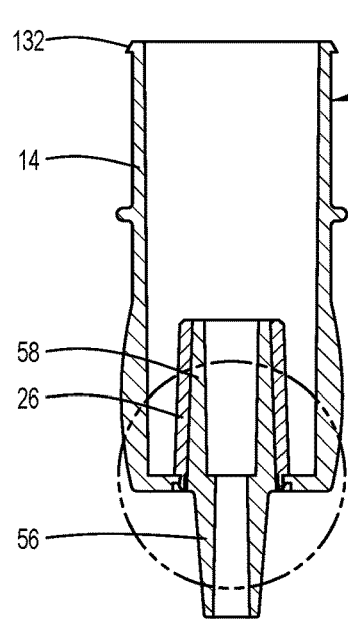
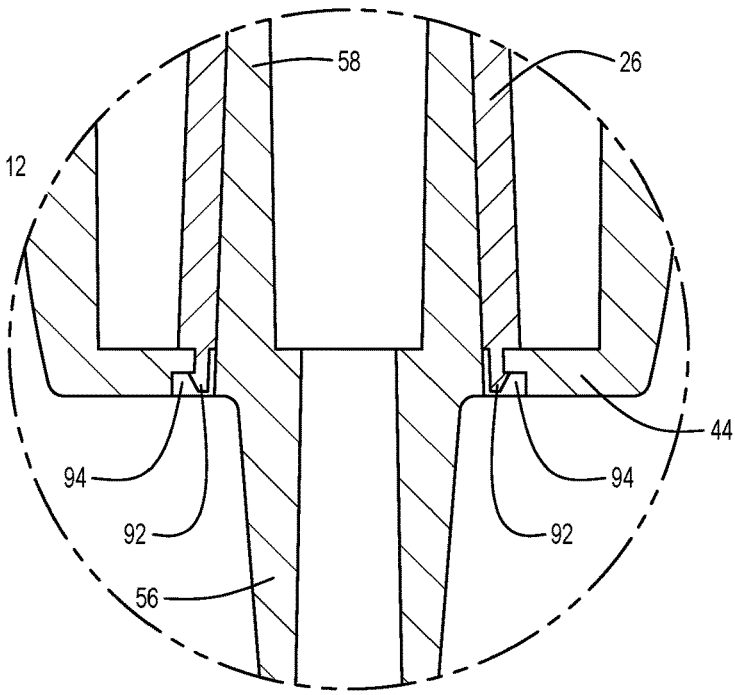
FIG. 35  FIG. 36

GAS FLOW INDICATOR DEVICE

CROSS-REFERENCE

This application claims the benefit of Australian Provisional Patent Application No.: 2017902508, filed on 28 Jun. 2018, the entire contents of which is incorporated herein by reference thereto.

FIELD OF THE INVENTION

The present invention relates generally to gas monitoring device. More particularly, the present invention relates to gas flow indicator device for gas delivery devices or systems and gas supply conduits.

It will be convenient to hereinafter describe the invention in relation to gas flow indicator device for medical devices, systems or conduits that deliver breathing gas to an individual's airway. However, it is to be appreciated that the present invention is not limited solely to that use. For example, an alternative use for gas flow indicator device of the invention could include breathing gas delivery devices or systems and gas supply conduits for use in the aviation industry. Also, the gas flow indicator device of the invention could be used for other, non-breathing gas applications, and the invention should not be construed as limited to any one or more of the specific examples provided herein.

BACKGROUND OF THE INVENTION

Any discussion of documents, devices, acts or knowledge in this specification is included to explain the context of the invention. It should not be taken as an admission that any of the material forms a part of the prior art base or the common general knowledge in the relevant art in Australia, Europe, New Zealand, Malaysia, the United Kingdom, the United States of America or elsewhere, on or before the priority date of the disclosure herein.

Unless stated otherwise, throughout the ensuing description, "gas" or "gases" refers to any suitable gas, mixture of gases, vapour or a gas/vapour mixture that, as such, can be monitored using the gas flow indicator device of the invention. A gas with which the flow indicator device can be used can entrain an aerosol. In the context of medical or other respiratory applications of the gas flow indicator device, "gas" refers to any suitable breathing gas, generally oxygen, a mixture of oxygen and inert gas and/or pharmacological agent, air and oxygen-enriched air. Similarly, the expression "gas delivery device", "gas delivery system" or "gas delivery conduit" refers to any suitable device, system and conduit for supplying gas to, or at, a desired location such as, in the context of a medical or other respiratory application, to or into an individual's airway. Examples of suitable device, devices, systems or conduit include, but are not limited to facemasks, mouth pieces, nasal cannulas and gas supply conduits. For non-spontaneous breathing applications suitable device, devices, systems and conduits may include manual resuscitator devices, such as, for example, bag valve masks and endotracheal tubes.

Supplemental gas is widely used in the medical field. For example, supplemental oxygen is used to assist or maintain safe blood oxygen levels for a patient. The duration of supply of supplemental oxygen varies, depending on the condition of the patient and/or the particular circumstance necessitating supplemental oxygen being administered. Common scenarios include patients having cardio-respiratory diseases or dysfunctions and surgical/anaesthetic interventions that mandate supplementation of atmospheric air with higher concentrations of inspired oxygen in order to achieve normal oxygen tensions in the patient's blood. Failure to deliver supplemental oxygen can lead to risk of reduced arterial oxygen tension that, if not corrected, can contribute directly to increased morbidity and mortality.

Failure of supplemental gas delivery is an acknowledged and feared system risk in hospitals. To safeguard against this, more often than not there are multilevel complex alarms and flow sensors within the hospital's in-built gas piping circuitry, and/or at gas supply outlets provided throughout hospital facilities. In addition, anaesthetic machines, intensive care ventilators, or the likes, have mandatory flow sensors engineered into their design to detect and alert of gas supply failure.

The gas supply systems of most hospitals generally are monitored, from the source to the supply outlet. The same applies to complex anaesthetic machines and ventilators. However, the most commonly used, and often most simple, gas delivery devices, systems and conduits, are not provided with any effective gas flow indicator device. Hence, their use can lead to the failure of gas delivery going unnoticed. This risk is increased in situations involving gas supply from portable gas tanks or cylinders.

One of the most commonly used gas delivery devices for spontaneously breathing patients is the gas delivery facemask, or oxygen mask. Sometimes called the "Hudson Mask", with reference to the early mask innovations of the Hudson Company, most such masks are made of a clear plastics material and include a body that is sized to seat over the nose and mouth of a patient. With conventional mask designs, gas is introduced through a gas inlet, and expiratory gases are vented from either around the side of the mask or through appropriately placed ventilation apertures. Gas is supplied to the gas inlet from a gas supply source, commonly by way of a length of clear plastic conduit. The gas supply source may be an in-built hospital supply source, or a gas tank or cylinder.

Oxygen masks usually are designed to increase a patient's inspired fraction of oxygen, such as from about 21% to about 40%. The oxygen flow rate required to achieve this is about 6 litres per minute ("6 L/min"). When oxygen flow into the mask fails the prescribed inspired oxygen concentration is not achieved. Of greater concern, the patient re-breathes their expired gases which can't be replenished satisfactorily by entrainment of air around the side of the mask, ultimately leading to the inspiration of a gas mixture with a low level of oxygen (less than 21% oxygen) and a risk of hypoxemia. Oxygen masks are not presently provided with any visual indicator confirming the presence of oxygen flow into the mask, or in the oxygen supply conduit proximate the mask. With the use of a mask, it is not inherently obvious to a medical practitioner, to a carer or even to the patient when there is an insufficient or complete lack of oxygen flow. A visual inspection of the oxygen delivery system (e.g. conduit and mask) will not generally indicate whether or not oxygen is flowing. For this reason, medical practitioners often find it necessary to use audible cues as a means of identifying that there is a flow of oxygen. However, even putting ones ear or a stethoscope adjacent to a mask may sometimes still not make clear whether gas is flowing, and the medical practitioner still has no way of knowing whether oxygen is being supplied at the prescribed flow rate of oxygen, such as about 6 L/min.

For non-spontaneously breathing patients, one of the most commonly used manual resuscitator gas delivery devices is the bag valve mask or "BVM". Sometimes called the "AMBU" bag or mask, with reference to the proprietary name appointed by the inventors' of the original BVM, such devices consist of a flexible air chamber (the "bag") attached to a facemask or endotracheal tube via a shutter valve. When the mask is properly applied to a patient (or endotracheal tube is correctly inserted into the patients trachea) and the "bag" is squeezed, the device forces air into the patient's lungs. When the bag is released, it self-inflates from its supply end, drawing in either ambient air or oxygen supplied by an oxygen supply source, while also allowing the patient's lungs to deflate to the ambient environment (but not to the "bag") by way of a one-way expired air valve. The BVM generally includes two inlet ports for drawing in ambient air or oxygen. When available, oxygen is supplied to one of the inlet ports from a gas supply source, commonly by way of a length of clear plastic conduit. The gas supply source may be an in-built hospital supply source, or a gas tank or cylinder. The other inlet port can then be used to draw in ambient air, or to connect a reservoir for catching unused oxygen between compressions of the "bag". In case oxygen flow is not sufficient to fill the "bag", the reservoir generally includes a one-way valve for drawing in ambient air to ensure that the BVM continues to supply at least ambient air to the patient.

BVMs are designed to deliver up to 100% inspired oxygen to a patient. With a loss of supplemental oxygen supply into the "bag", the BVM will continue to entrain ambient air (with an oxygen concentration of about 21%) with which to ventilate the patient. However, patients requiring the use of such manual resuscitator devices often have severely compromised respiratory function, which means that they require much higher inspired oxygen concentrations than that of ambient air. Therefore, any loss of supplemental oxygen supply can have catastrophic sequelae if undiagnosed. As with the case of the common oxygen mask described above, loss of oxygen supply to a BVM can be, and often is, missed as there is presently no visual flow indicator device provided at or proximate the BVM confirming supplemental oxygen inflow. Again, although the presence of a sound may indicate that gas is flowing, the medical practitioner still has no way of knowing whether the required flow rate of oxygen is present at the BVM.

Often gas tanks or cylinders are used to supply oxygen to masks or BVM's, most commonly in emergency, perioperative, critical care or transport scenarios. While some cylinders do have ball-type flow indicators at their supply outlets, the cylinders are often placed in positions in which they are visually obscured, such as under a patient's bed or transportation trolley, or placed side-ways rendering the ball-type flow indicators inaccurate. Additionally, most cylinders do not have alarms in the event of cylinder oxygen supply running empty during use to indicate oxygen supply failure. Even more concerning is that newer designs of oxygen cylinders commonly no longer have ball-type or other flow indicator incorporated into their design. Hence, failure of supply of supplemental gas to gas delivery devices or systems is a real and likely problem.

One substantial advance in the art is provided by the gas flow indicator device disclosed in our International Patent Application No.: PCT/AU2013/000884, published under WO 2014/026221 A1 on 20 Feb. 2014, and its counterparts in Australia (Patent/Application Nos.: 2013302298 & 2017261637), Europe (Application No.: 13829326.1), New Zealand (Patent/Application Nos.: 705892 & 732790) and the United States of America (application Ser. No. 14/421, 039). The gas flow indicator device of those patents/applications comprises a gas flow chamber including a transparent portion and an opaque portion, an inlet port, an outlet port, and a gas flow signal means movably disposed within the gas flow chamber; wherein, when there is no gas flow or less than a predetermined gas flow rate, the gas flow signal means is disposed at least substantially within one of the transparent portion and the opaque portion; and wherein, when there is gas flow and the predetermined gas flow rate has been achieved or is being maintained, the gas flow signal means is moved to be disposed at least substantially within the other of the transparent portion and the opaque portion. Typically, the gas flow signal means is biased to a rest position substantially within the one of the transparent and opaque portions and includes a bellows device or a piston device.

Our Australian Patent Application No.: 2016277769, filed on 29 Dec. 2016 (and its counterparts in Europe (Application No.: 16207372.0), New Zealand (Application No.: 727977), the United States (application Ser. No. 15/393, 404), and International Patent Application No.: PCT/AU2016/051296), describes a gas flow indicator device that provides a further substantial advance. At least in preferred embodiments, Australian Patent Application No.: 2016277769 (and its counterparts) provides a device that enhances visual recognition of required gas flow by its indicator portion being visible through a viewing window at which the indicator portion is seen as magnified.

While the gas flow indicator devices of our earlier patents/applications identified above work effectively and are reliable, they are either relatively complex and require careful attention to detail during manufacture, or they have been found to omit noise during use, or can be difficult to fit to a facemask or the likes. The present invention is concerned with providing a further improved form of gas flow indicator device.

DISCLOSURE OF THE INVENTION

Accordingly, in one aspect, the present invention provides a gas flow indicator device including:

(a) an elongate housing that has a peripheral sidewall that extends between first and second opposite ends and that defines a gas flow chamber through which gas is able to flow from an inlet port at a first end to an outlet port at a second end;

(b) a gas flow indicator member within the chamber that extends from adjacent to the first end of the housing over part of the length of the chamber towards the second end, with the indicator member being of annular form such that gas flowing through the chamber from the inlet port to the outlet port enters the chamber along a bore that extends through the indicator member and with the indicator member spaced from an inner surface of the sidewall of the housing to define, with that inner surface, an annular space that forms part of the chamber;

(c) a concealment member that is movable from the first end of the housing in response to a sufficient pressure generated by gas flow from the inlet port to the outlet port, against the action of a biasing member acting to bias the concealment member to the first end, the concealment member having an annular peripheral skirt that, under the bias of the biasing member on the concealment member, is receivable into the annular space, such that one of opposite ends of the skirt is able to seal against an annular surface of the housing at or adjacent to an end wall of the housing at the first end of the housing, with the concealment member also including, at the other of the opposite end of the skirt, a transverse wall that defines an opening through which the flow of gas from the inlet port to the outlet port is able to pass, with the opening providing resistance to such flow; and, (d) with the arrangement such that the one of opposite ends of the skirt is able to be held in sealing engagement with the annular surface at or adjacent to the end wall of the housing whereby the indicator member is concealed or obscured from view, through a laterally adjacent viewing window portion of the housing, when there is no gas flow or a gas flow rate generating less than the sufficient pressure but such that, with increasing gas flow rate the sufficient pressure is achieved and the bias of the biasing member is thereby overcome to enable the concealment member to move towards the second end of the housing and expose the indicator member to view through the viewing window portion of the housing and provide a visual indication indicative of gas flow.

At least in preferred forms, the device of the present invention includes a fitting member mounted at the second end of the elongate housing. The fitting member has a rim, a hub disposed within the rim and circumferentially spaced connectors by which the rim is connected to the hub, with a respective opening defined between the rim and the hub and between successive pairs of the circumferentially spaced connectors. The rim has an annular wall portion that, with the fitting member mounted on the second end of the housing, abuts against or is closely adjacent to an end surface of the second end of the housing, with the connectors extending to the hub from an inner periphery of the annular wall portion. The rim also has an annular skirt portion extending around and from the outer periphery of the annular wall portion such that, with the fitting member mounted on the second end of the housing, the skirt portion fits securely onto an end margin of the outer surface of the housing. From the hub and connectors, the fitting member has an axially extended engagement portion such that, with the fitting member so mounted on the housing, the engagement portion projects beyond a free edge of the skirt portion that is spaced from the wall portion, with the engagement portion spaced from the inner surface of the housing. That is, the engagement portion preferably has an axial extent or length from the wall portion of the rim that exceeds an axial extent or width of the skirt portion from the wall portion. The axial extent of the engagement portion may be such that the engagement portion may extend beyond the free edge of the skirt portion by 1.5 to 4 times greater than a spacing of the free edge of the skirt portion from the wall portion sufficient to enable the skirt portion to grip the housing for retaining the fitting member in relation to the housing. As a consequence, the axial extent or length of the engagement portion able to project into the housing is such that a number of beneficial arrangements are enabled.

The fitting member of the present invention primarily is applicable to a biasing member acting in compression, even though it can be used with a biasing member acting in tension. With a biasing member acting in compression, the engagement portion of the fitting member may engage an end of the biasing member that is remote from the concealment member. Thus, in the case of a biasing member in the form of a coil or helical spring, one form of the fitting member mountable on the second end of the housing has an engagement portion that is engaged with the end of the spring that is remote from the concealment member. The engagement portion may fit within, and restrict movement of, the remote end of the spring, with the engagement portion preferably being a neat fit within the remote end. The engagement portion may limit, or substantially preclude, movement of the remote end of the spring laterally with respect to the inner surface of the housing, or longitudinally away from the concealment member, or both laterally with respect to the inner surface of the housing and longitudinally away from the concealment member. In any event, the engagement portion preferably engages the remote end on the spring at a location spaced from the wall portion of the rim of the fitting member, most preferably a location spaced from the wall portion beyond the free edge of the skirt portion of the rim.

In one arrangement, the hub and at least some of the connectors are extended to define the axially extending engagement portion. The arrangement may provide an engagement portion in the form of an axially extending fin, or an engagement portion of a star-shape in transverse cross-sections, such as a tri-star or cruciform star shape. The fins may taper so as to decrease in cross-section towards a free end remote from the wall portion of the rim. Alternatively, each fin may have an outer edge that is stepped intermediate of its ends to define a shoulder facing towards the free end and an end portion between the shoulder and the free end that is of reduced cross-section relative to a remaining portion. In each case, an end portion of the engagement portion is able to be received within the end of the spring remote from the concealment member, preferably as a neat fit in the end of the spring, and thereby bring the engagement portion into engagement with that end of the spring.

Alternatively, the engagement portion may be of a tapered or frusto-conical form that decreases in cross-section in a direction away from the wall portion of the rim. Thus, the engagement portion may have a free end that is spaced from the wall portion and is received within the remote end of the coil or helical spring, with the taper of the engagement portion relative to the diameter of the spring resulting in an interference fit between the remote end of the spring and a location intermediate of opposite ends of the engagement portion that limits the extent to which the engagement portion is able to be received within the spring. In that manner, the engagement portion provides an abutment that restricts movement of the spring. However, in an alternative arrangement, the engagement portion may provide an abutment for that purpose by being stepped intermediate of its ends, to provide a free end portion of lesser, preferably substantially uniform, cross section than a remainder portion nearer to the wall portion of the rim, with an annular abutment shoulder being defined at the step. Thus, in that alternative arrangement, the free end portion of the engagement portion is able to be received, preferably as a neat fit, within the remote end of the spring to limit or substantially preclude lateral movement of that remote end, such that the shoulder provides an abutment against which the remote end of the spring bears thereby to restrict or substantially preclude longitudinal movement of that remote end.

In preferred arrangements of Australian Patent Application No.: 2016277769 (and its counterparts) for gas flow devices having a coil or helical spring acting in compression, the end of the spring remote from the concealment member is abutted, at the outlet end of the housing, against a fitting member that has a rim, a hub and circumferentially spaced connectors by which the rim is connected to the hub. However, the hub is of without axial extent beyond a wall portion of the rim and the end of the spring remote from the concealment member abuts against the wall portion of the rim or the connectors by which the rim is connected to the hub. That arrangement is suitable for most purposes, although two difficulties can occur, at least under some in-use conditions such as higher gas flow rates. The first is that the remote end of the spring can vibrate, resulting in a distracting sound. The second is that, if the spring is caused to compress fully, so that successive coils are in contact, the spring can be substantially fully compressed to form a substantially continuous cylinder that can severely restrict or even substantially impede the flow of gas. These difficulties can be avoided by careful attention to manufacturing tolerances and the spring rate of the coil or helical spring. However, the fitting member of the present invention more positively obviates these issues by constraining the remote end of the spring against lateral movement enabling it to vibrate, while extension of the engagement portion into the remote end of the spring enables the extent of compression of the spring to be limited so as to preclude contact between successive coils of the spring.

The fitting member of the present invention may have an extension portion that, with the fitting member mounted on the second end of the housing, is external with respect to the housing. The extension portion may comprise an annular part of the rim that extends from the wall portion of the rim, in a direction away from the free edge of the skirt portion of the rim. The extension portion may have a tapered or frusto-conical outer periphery that decreases in transverse or lateral cross-sections in a direction away from the wall portion of the rim and, where this is the case, the taper may assist with insertion of the gas flow indicator device into a socket defined in a facemask with which the device may be used. The openings between successive connectors by which the rim is connected to the hub preferably extend through the extension portion. Also, the hub and connectors and, hence, the openings preferably extend to a free edge of the extension member.

In one convenient preferred arrangement, the concealment member is made of an opaque material through which the indicator member is not able to be seen when the one end of the skirt of the concealment member is held in sealing engagement with the annular surface at or adjacent to the end wall of the housing. When the concealment member is moved to expose the indicator member, the outer surface characteristics of the indicator member can be seen by being directly viewed and, as detailed herein, those characteristics preferably are such as to highlight exposure of the indicator member after movement of the concealment member. However, the concealment member need not be opaque in order to make possible its concealment, obscurity or exposure of the indicator member. Thus, the concealment member may be semi-opaque, translucent or even transparent but of a material of a colour that interacts with the colour of the indicator member in a visually distinctive manner resulting in an observer being able to readily distinguish between a condition in which the actual colour of the indicator member is concealed or obscured, or only visible through the concealment member and seen as if of a colour other than its actual colour, and a condition in which the actual colour of the indicator member can be seen by direct viewing made possible by the concealment member being withdrawn or retracted by a sufficient gas flow rate moving the concealment member against the action of the bias member.

As already indicated, the biasing member may act in compression or in tension in biasing the concealment member to the first end of the housing. Thus, the biasing member may be compressed between, such as compressed by, the concealment member and the second end and provide the required bias in seeking to expand. Alternatively, the biasing member may be within the concealment member, and tensioned by being expanded between, such as by being connected in relation to, each of the transverse wall of the concealment member and the first end of the housing so as to provide the bias in seeking to contract. While other arrangements are possible, the biasing member preferably comprises a coil spring in each of those alternatives.

Where the biasing member is a coil or helical spring acting between the concealment member and the second end of the housing, compression of the spring can limit the extent to which the concealment member can move towards the second end of the housing simply as a consequence of the presence of the compressed spring. Where the biasing member is a coil spring within the concealment member, the arrangement may be such that the concealment member is able to move so as to contact the end wall at the second end of the housing, although the arrangement may be such that contact of the concealment member with the second end of the housing is precluded by the spring reaching its elastic limit.

The concealment member preferably is able to move, between a first position in which the indicator member is concealed or obscured and a second position in which the indicator member is sufficiently exposed, or fully or substantially fully exposed, over a distance enabling a clear visual indication of gas flow through the device. The arrangement is such that, when so exposed, the indicator member can readily be seen through the viewing window portion of the sidewall of the housing by a person in close proximity, such as beside the bed of a patient being supplied oxygen through the device, and preferably also from a considerable distance such as from five to ten metres, or further, from the device. In order that the indicator member is viewable, the viewing window portion is at least translucent. However, the window portion preferably is sufficiently transparent to facilitate viewing of the indicator member, when exposed. The viewing window portion most preferably is of high transparency. Also, the viewing window portion most preferably extends around the full circumferential extent of the sidewall of the housing adjacent to the first end, although it could comprise two or more regions spaced circumferentially around that sidewall of the housing adjacent to the first end. Particularly where the viewing window portion extends around the full circumferential extent of the sidewall of the housing, it preferably is of a high-transparency plastics or glass material, with the material preferably also having a high level of clarity. The laterally adjacent portion of the housing, particularly where the viewing window portion extends fully around the circumferential extent of the sidewall of the housing, may be of a different material to that of a remaining extent of the length of the housing and, in that case, the material of which the remainder of the housing is made may be transparent, translucent or opaque, as required. However, the housing preferably is of unitary or integral form and made of a single material, preferable a rigid plastics material such as a suitable engineering plastics material. Where the housing is of unitary or integral form, and made of a transparent material, the remainder of the housing may be rendered opaque or semi-opaque by provision of an external or internal lining or coating of an opaque material.

The housing may be of circular in cross-sections perpendicular to the direction of spacing between the first and second ends. The inner surface of the sidewall of the housing may be substantially cylindrical and of substantially constant circular transverse cross-section between the first and second ends, while the sidewall also may have an outer surface that is substantially cylindrical and of substantially constant circular cross-section. However, for reasons explained later herein, the outer surface of the sidewall may depart from such cylindrical form, at least along an initial section of its longitudinal extent from adjacent to the first end, with that initial section extending around the gas flow indicator member. In one convenient arrangement, the outer surface of the sidewall, over that initial section of its longitudinal extent, may smoothly increase in diameter to a maximum in a direction away from the first end towards the second end, and thereafter transition to smoothly decrease in diameter substantially to the diameter at the first end, so as to have a convex longitudinal form. The at least one viewing window portion discussed above preferably has such convex longitudinal form, with the portion of that form most preferably being circumferentially continuous around the housing.

At the first end of the housing, the inlet port may be defined by a spigot that projects from the first end of the housing in a direction away from the second end, and that enables connection of a gas supply conduit to the housing. In one arrangement, the spigot may have an extension into the interior of the housing to provide a tubular extension or hub which may act as the indicator member, or on, within or around which the gas flow indicator member can be mounted or otherwise provided (i.e. by provision of an external or internal lining or coating, etc.). In the arrangement where the indicator member is mounted on the hub, the indicator member may have an axial extent that is substantially the same as, or slightly greater than, the length of the hub. The indicator member may be a firm friction fit on the hub so as to secure the indicator member in position and, to assist in attaining a firm fit, the indicator member and the hub may have complementary surfaces by which they are mutually engaged. The surfaces may taper so as to decrease in cross-section towards the outlet end, for example frusto-conically. The taper preferably is relatively slight, such as with a half-cone angle of about two to about six degrees. However other arrangements are possible. For example, the indicator member may be bonded or welded onto the hub, without the need for a friction fit. Alternatively, the indicator member may have an end, adjacent to the end wall at the first end of the housing, by which the indicator member is bonded or welded to the end wall. In a further alternative, the indicator member may have, at its end remote from the first end of the housing, a flange that overlaps the corresponding end of the hub, with the flange bonded or welded to that end of the hub. However, in another arrangement, the spigot does not have an extension that projects into the housing, with the indicator member being bonded or welded to the end wall of the housing at the first end, or mechanically engaged with that end wall such as by screw-threaded engagement or a snap fit in or around the inlet port.

The skirt of the concealment member preferably has an outer surface that is spaced from the inner surface of the sidewall of the housing, although relative sliding contact may be provided between those surfaces. Where there is spacing between the surfaces, this most preferably applies throughout the extent of movement of the concealment member longitudinally within the housing. The inner surface of the sidewall of the housing preferably is of substantially uniform circular cross-section. The device may have guide members that maintain the concealment member in a substantially co-axial relationship with the housing. Such guide members may comprise a plurality of circumferentially spaced projections that stand proud, or project inwardly, of the inner surface of the housing so as to be contactable with the outer surface of the skirt of the concealment member. In one convenient form, the guide members are provided by a plurality of longitudinal ribs on the inner surface of the sidewall of the housing, with three or four such ribs usually being sufficient. In an alternative arrangement, the plurality of guide members may stand proud, or project outwardly, of the outer surface of the skirt of the concealment member. In either case, the outer surface of the skirt of the concealment member may be of substantially uniform circular cross-section, although it preferably has a slight taper so as to decrease in cross-section towards the other end at which the transverse wall of the concealment member is provided, such as a taper providing a half-cone angle of from about two to about six degrees. The guide members not only centralise the concealment member, but also preferably obviate noise or vibrations due the concealment member rattling or oscillating laterally within the housing.

The inner surface of the skirt of the concealment member, when the indicator member is concealed or obscured, preferably is spaced from the outer peripheral surface of the indicator member. This avoids contact between the skirt of the concealment member and the indicator member, and thereby obviates friction that could resist movement of the concealment member relative to the indicator member. The skirt of the concealment member and the indicator member each may be of uniform wall thickness along its respective axial extent, while they may be of similar or substantially the same wall thickness.

According to a further aspect, the present invention provides a gas delivery device, gas delivery system or gas supply conduit including the gas flow indicator device of any one of the preceding paragraphs.

These and other essential or preferred features of the present invention will be apparent from the description that now follows.

BRIEF DESCRIPTION OF THE DRAWINGS

In order that the invention may be more clearly understood and put into practical effect there shall now be described in detail preferred constructions of a gas flow indicator device for gas delivery devices or systems and gas supply conduits in accordance with the invention. The ensuing description is given by way of non-limitative examples only and is with reference to the accompanying drawings, wherein:

FIGS. 8 and 9 correspond to views FIGS. 4 and 5, respectively, but in exploded views on an enlarged scale;

FIGS. 14 and 15 correspond to FIGS. 6 and 7, respectively, but with one component sectioned to better illustrate internal components;

FIGS. 16 to 18 show different preferred forms for one component of the device of FIG. 2;

FIG. 19 shows the device of FIG. 2, in a view corresponding to FIG. 6, as incorporated into a conduit flow-line;

FIG. 20 corresponds to FIG. 19, but shows the device and flow-line in longitudinal section;

FIGS. 21 to 24 illustrate a gas flow indicator device according to a second embodiment of the invention, shown in views corresponding to FIGS. 6, 11, 13 and 10, with FIGS. 22 and 23 taken on line Y-Y of FIG. 24;

FIGS. 29 to 36 provide respective sectional views illustrating alternatives for securing together two components for the device of the illustrated first or second embodiments of the invention shown in FIGS. 2 to 20 and FIGS. 21 to 24 respectively;

MODES FOR CARRYING OUT THE INVENTION

Figure 1:
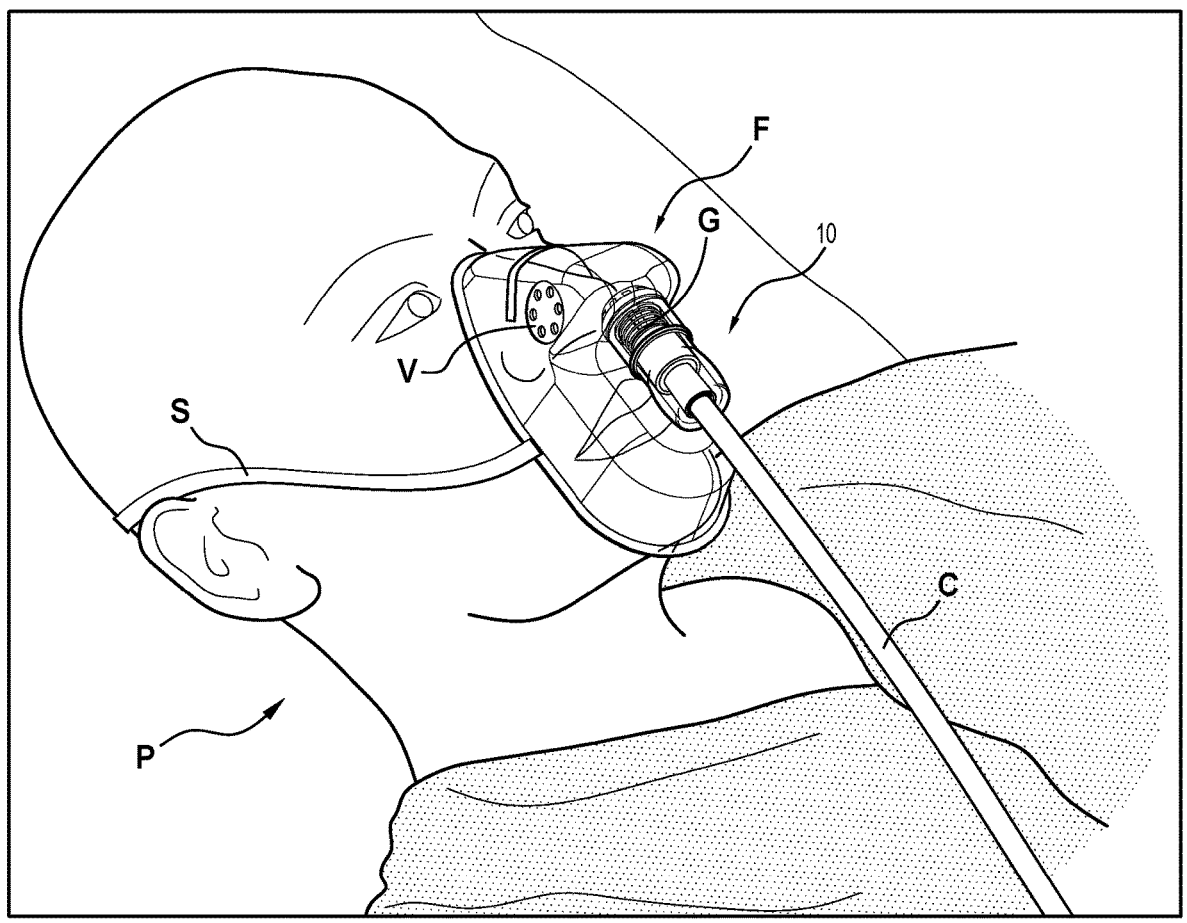
FIG. 1 is a schematic representation of gas flow indicator device according to the invention as incorporated into a facemask installed on a patient to receive a controlled gas supply.
Figure 2:
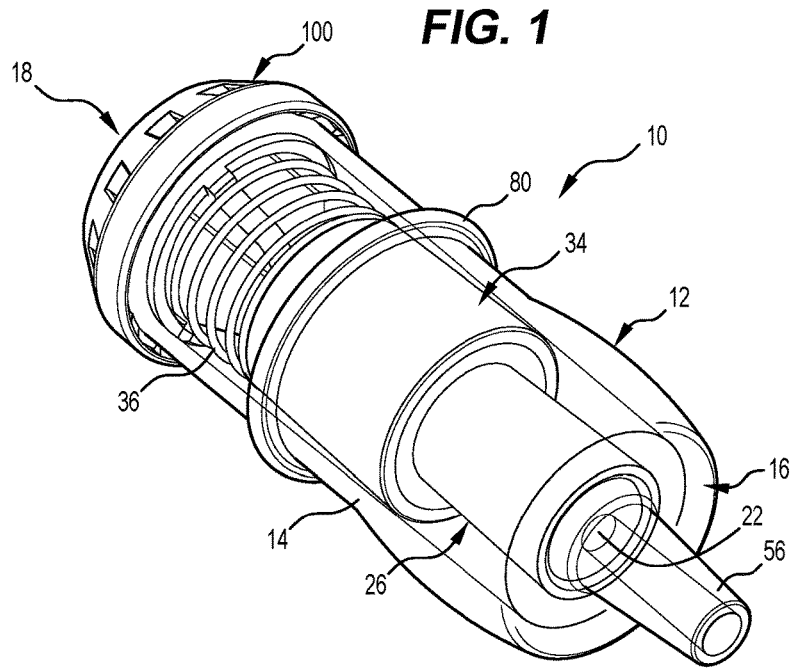
FIG. 2 shows a perspective view of a first preferred embodiment of a gas flow indicator device according to the invention, shown in an operating condition.

In the following detailed description of the invention, reference is made to the drawings in which like reference numerals refer to like elements throughout, and which are intended to show by way of illustration specific embodiments in which the invention may be practiced. It is to be understood that other embodiments may be utilised and that procedural and/or structural changes may be made without departing from the spirit and scope of the invention.

FIG. 1 schematically illustrates a patient P undergoing a procedure in which the patient P is receiving a controlled supply of required gas through a gas flow indicator device 10. The device 10 is fitted into a facemask F held by strap S over the nose and mouth of the patient P and the required gas is passed to the device 10 from a source of supply (not shown) via a conduit C.

Figure 3:
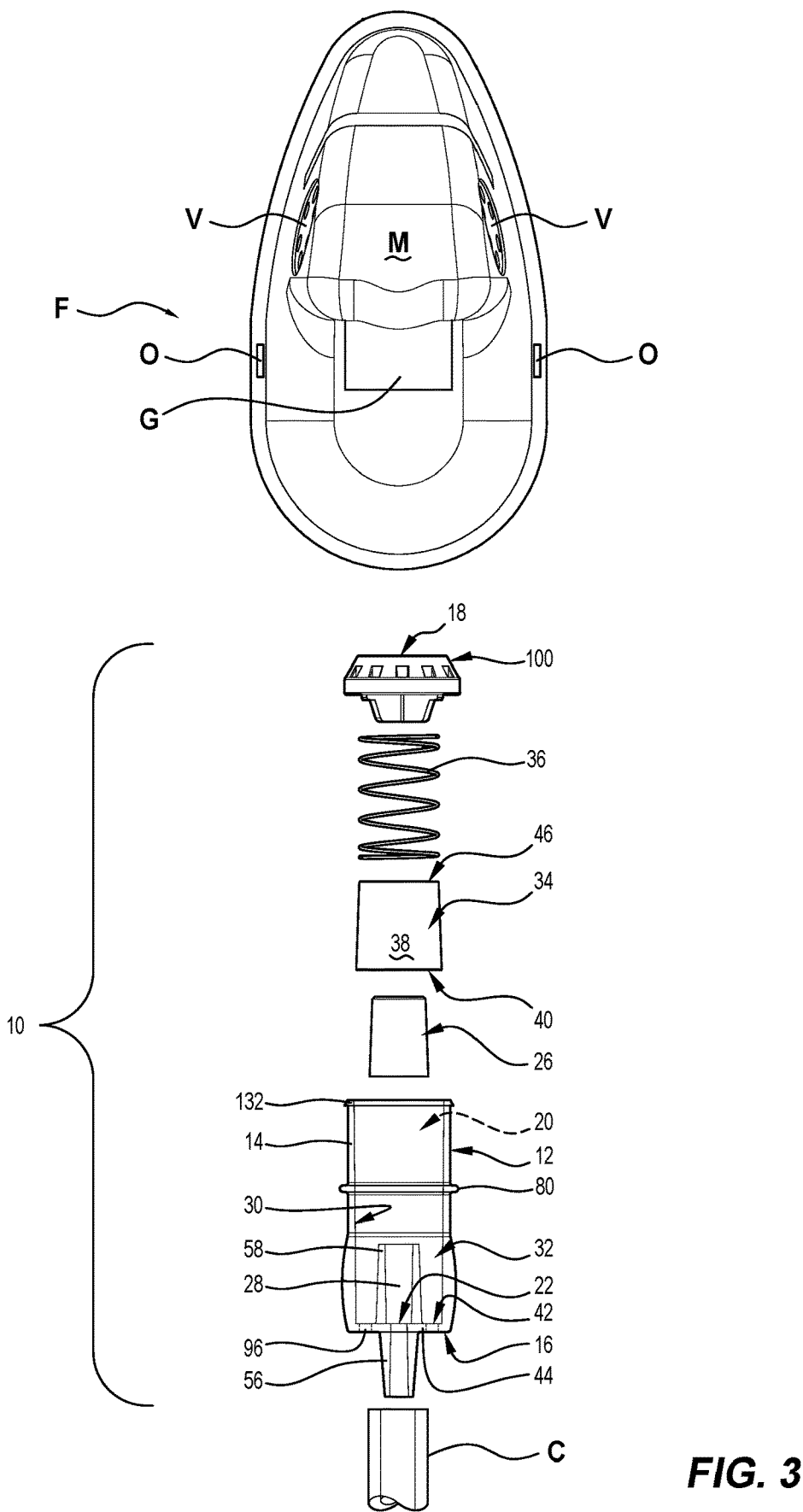
FIG. 3 is an exploded view of the device of FIG. 2, shown in a non-operating condition in relation to a facemask.
Figure 4:
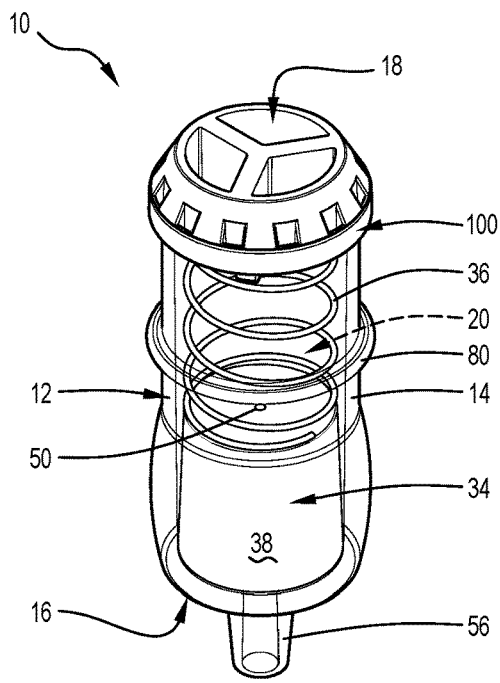
FIG. 4 is perspective view from one end of the device of FIG. 2, this time shown in a non-operating condition.
Figure 5:
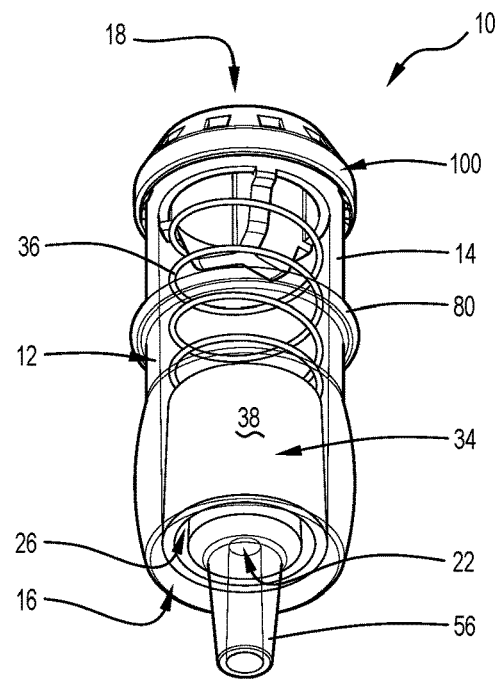
FIG. 5 is similar to FIG. 4 but taken from the other end.
Figure 6:
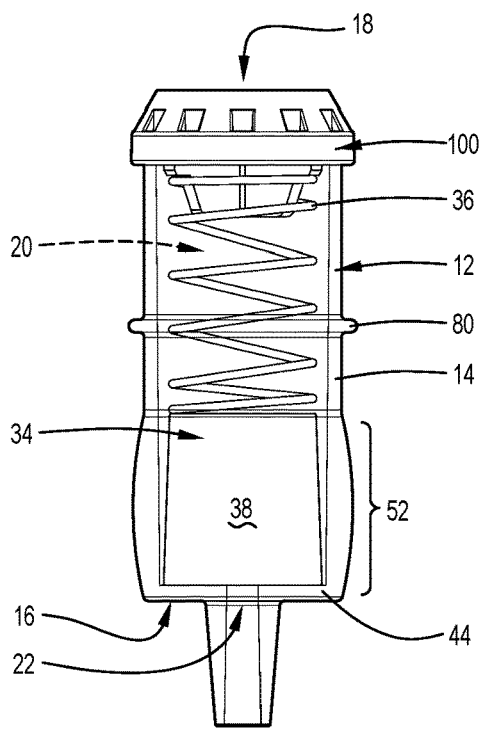
FIG. 6 is a side elevation showing the device of FIG. 2 in the non-operating condition applicable to each of FIGS. 4 and 5.
Figure 7:
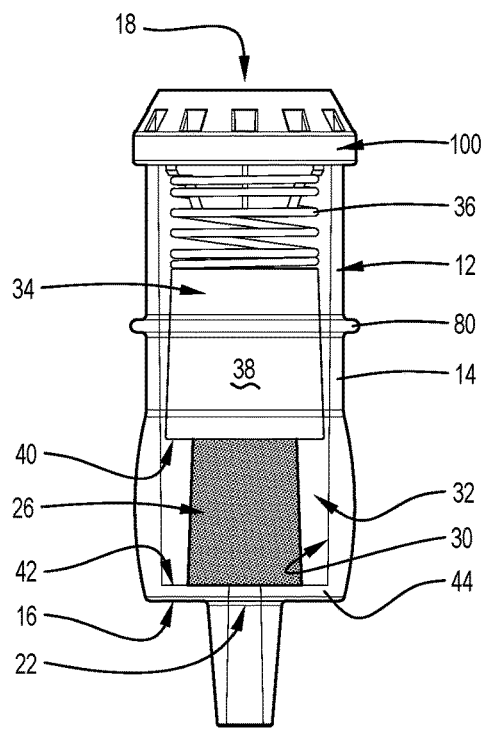
FIG. 7 corresponds to FIG. 6, but shows the device in its operating condition.
Figure 10:
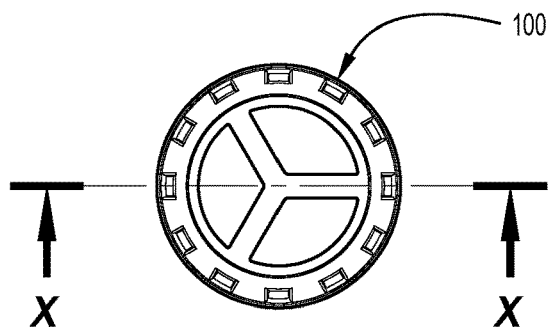
FIG. 10 is a plan view from one end of the device of FIG. 2.
Figure 11:
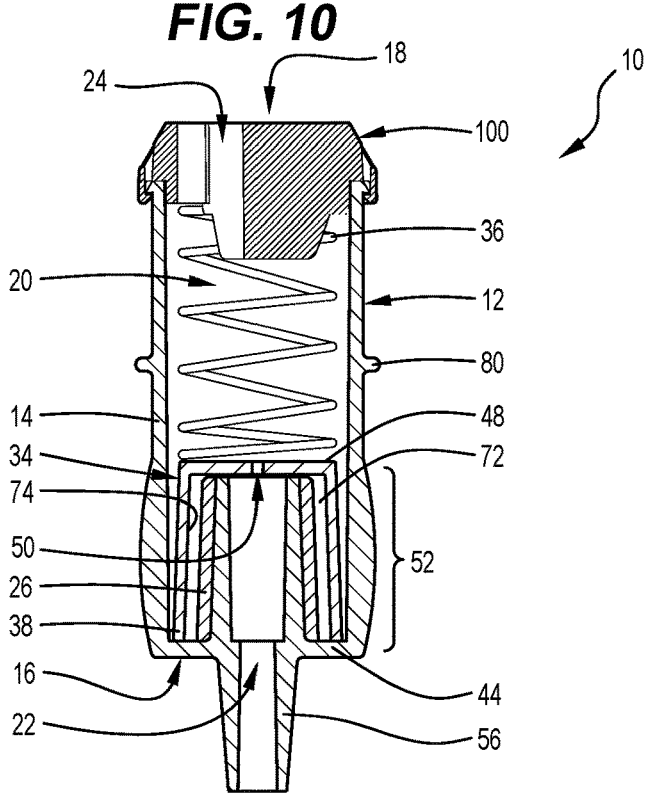
FIG. 11 is a sectional view of the device of FIG. 2, taken on line X-X of FIG. 10.
Figure 12:
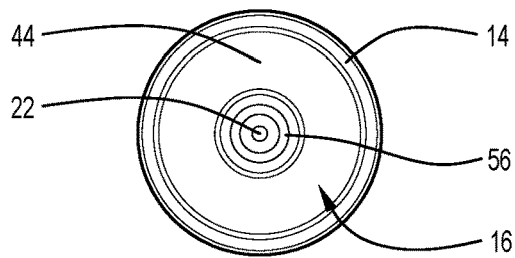
FIG. 12 corresponds to FIG. 10, but is taken from the opposite end.

The device 10 comprises a gas flow indicator device that, as shown in FIGS. 2 to 15, is of elongate form. Device 10 includes an elongate housing 12 that, as shown in FIG. 3, has a peripheral sidewall 14 that extends between first and second opposite ends comprising an inlet end 16 and an outlet end 18, respectively. The housing 12 defines a gas flow chamber 20 through which gas is able to flow from an inlet port 22 at the inlet end 16 to an outlet port 24 (see, for example, FIG. 11) at the outlet end 18. Within the chamber 20 the device 10 has a gas flow indicator member 26 that extends from adjacent to the inlet end 16 of the housing 12 over part of the length of the chamber 20 towards the outlet end 18, typically less than half the length of the chamber 20, such as from 35 to 45% of the length. The indicator member 26 is of annular form such that gas flowing through the chamber 20 from the inlet port 22 to the outlet port 24 enters the chamber 20 along a bore 28 that extends through the indicator member 26. The indicator member 26 is spaced from an inner surface 30 (see, for example, FIG. 7) of the sidewall 14 of the housing 12 to define, with that inner surface 30, an annular space 32 (again, see for example, FIG. 7) that forms part of the chamber 20.

The device 10 has a concealment member 34 that is movable from the inlet end 16 of the housing 12 in response to a sufficient pressure generated by gas flow from the inlet port 22 to the outlet port 24. However, such movement of concealment member 34 is against the action of a biasing member 36 acting to bias the concealment member 34 to the first end 16 of housing 12, with the biasing member 36 reacting between and held in compression by, concealment member 34 and a fitting member 100 (described later herein) that is secured at the second, outlet end 18 of housing 12. The concealment member 34 has an annular peripheral skirt 38 that is receivable into the annular space 32, such that one end 40 of the skirt 38 is able to seal against an annular abutment surface 42 defined by housing 12 at or adjacent to an end wall 44 of the housing 12 at the inlet end 16 of the housing 12. The concealment member 34 also includes, at the other end 46 of the skirt 38, a transverse wall 48 that defines an opening 50 through which the flow of gas from the inlet port 22 to the outlet port 24 is able to pass, with the opening 50 providing resistance to such flow. The arrangement is such that the end 40 of the skirt 38 is able to be held in sealing engagement with the annular abutment surface 42 of the housing 12 whereby the indicator member 26 is concealed or obscured from view, through a laterally adjacent viewing window portion 52 of the housing 12 that is at least translucent until, with increasing gas flow rate, the sufficient pressure is achieved and the bias of the biasing member 36 is thereby overcome to enable the concealment member 34 to move towards the outlet end 18 of the housing 12 and expose the indicator member 26 to view through the viewing window portion 52 of the housing 12 and provide a visual indication indicative of gas flow. It is preferred that full exposure of the indicator member 26 shows that not only is gas flowing, but also that a desired or minimum predetermined flow rate, such as a flow rate of about 6 L/min, has been achieved and is being maintained. The movement of the concealment member 34 to expose the indicator member 26 moves the end 40 of the skirt 38 of the concealment member 34 from the annular abutment surface 42 of the housing 12, and most preferably thereby enables a secondary gas flow to the outlet port 24 that passes around the end 40 of the skirt 38 between the concealment member 34 and the housing 12 (as will be described in further detail below, with reference to FIG. 13).

In the arrangement of FIGS. 2 to 15, the biasing member 36 is a coil spring that acts in compression in acting to bias the concealment member 34 to the inlet end 16 of the housing 12. Although the use of coil spring is described, and shown in the drawings, it will be appreciated that any suitable form of biasing member 36 may be utilised in accordance with the invention. As is shown in FIGS. 2 to 20, the preferred coil spring biasing member 36 may be compressed by and between the concealment member 34 and the outlet end 18 of the housing 12 so as to provide the required bias in seeking to expand. The concealment member 34 is able to move against the bias from the position shown FIGS. 4 to 6, in which the indicator member 26 is concealed or obscured, to the position shown in FIGS. 2 and 7 in which the indicator member 26 is sufficiently exposed, over a distance enabling a clear visual indication of gas flow through viewing window portion 52 of the housing 12 of the device 10. The arrangement is such that, when exposed, the indicator member 26 can readily be seen through the laterally adjacent viewing window portion 52 of the sidewall 14 of the housing 12 by a person in close proximity, such as beside the bed of patient P of FIG. 1, and preferably also from a considerable distance such as from five to ten metres, or further, from the device 10 provided for patient P. Thus, the arrangement of device 10 is such that its operating condition can be readily determined, such as with only a quick glance being all that is required to obtain confirmation of the operation condition. The arrangement is such that device 10 is readily able to function, in effect, as if in the nature of an "on" or "off" switch, indicating respectively that there is, or there is not, gas being supplied to a patient P (preferably at a desired or minimum flow rate, e.g. such as about 6 L/min).

While the laterally adjacent viewing window portion 52 is at least translucent, it preferably is transparent to facilitate viewing of the indicator member 26, when exposed. The viewing window portion 52 most preferably is of high transparency, and most preferably extends around the full circumferential extent of the sidewall 14 of the housing 12 adjacent to the first end 16, as shown in each of FIGS. 2 to 15. However, such window portion could comprise two or more regions spaced circumferentially around sidewall 14. Particularly where the viewing window portion 52 extends around the full circumferential extent of the sidewall 14, it preferably is of a high-transparency plastics or glass material, with the material preferably also having a high level of clarity. The laterally adjacent viewing window portion 52, particularly where it extends fully around the circumferential extent of the sidewall of the housing 12, may be of a different material to that of a remaining extent of the length of the housing 12 and, in that case the material of which the remainder of the housing 12 is made may be transparent, translucent or opaque, as required. However, the housing 12 preferably is of unitary or integral form and made of a single material, preferable a rigid plastics material such as a suitable engineering plastics material.

The housing 12 is of circular in cross-sections perpendicular to the direction of spacing between the inlet and outlet ends 16 and 18, of device 10. The inner surface 30 of the sidewall 14 of the housing 12 may be substantially cylindrical and of substantially constant circular transverse cross-section between the first and second ends 16 and 18, while the sidewall 14 also may have an outer surface that is substantially cylindrical and of substantially constant circular cross-section. However, as shown in each of FIGS. 2 to 15, for reasons explained later herein with reference to FIGS. 37 and 38, the outer surface 54 of the sidewall 14 departs from such cylindrical form along an initial section of its longitudinal extent from adjacent to the first end 16, that substantially corresponds to the viewing window portion 52. Over that initial section, the outer surface 54 of the sidewall 14 smoothly increases in diameter to a maximum in a direction away from the inlet end 16 towards the outlet end 18, and thereafter smoothly decreases in diameter substantially to the diameter at the first end 16, so as to have a convex longitudinal form. The convex longitudinal form most preferably is circumferentially continuous around the housing 12.

The inlet port 22 is defined by a spigot 56 that projects from the inlet end of the housing 12 in a direction away from the outlet end 18, with the spigot 56 enabling connection of device 10 to a gas supply conduit C. As is shown in the drawings, the spigot 56 may have an extension that projects into the interior of the housing 12 to provide a tubular hub 58 on, within or around which the gas flow indicator member 26 may be securely mounted or otherwise provided (i.e. by provision of an external or internal lining or coating, etc.—not shown). Although not shown in the drawings, it will be appreciated that the tubular hub 58 may in itself define or provide indicator member 26 (or at least part thereof). In a preferred arrangement wherein the indicator member 26 is mounted on hub 58, the indicator member 26 may have an axial extent that is substantially the same as, or slightly greater than, the length of the hub 58. The indicator member 26 may be a firm friction fit on the hub 58 so as to secure the indicator member 26 in position and, to assist in attaining a firm fit, the indicator member 26 and the hub 58 may have complementary surfaces by which they are mutually engaged. The surfaces may taper so as to decrease in cross-section towards the outlet end 18, for example frustoconically, such as with a half-cone angle of about two to about six degrees. Alternatively, the indicator member 26 may be bonded or welded onto the hub 58, without the need for a friction fit. In a further alternative, the indicator member 26 may have an end adjacent to the end wall 44 at the inlet end 16 of the housing 12, by which the indicator member 26 is bonded or welded to the end wall 44. In another alternative, the indicator member 26 may have, at its end remote from the inlet end 16 of the housing 12, a flange that overlaps the corresponding end of the hub 58, with the flange bonded or welded to that end of the hub 58. However, in another arrangement (not shown), the spigot 56 does not have an extension that projects into the housing, in which case the indicator member 26 may be bonded or welded to the end wall 44 of the housing 12, or mechanically engaged with that end wall 44 such as by screw-threaded engagement or a snap-fit in or around the inlet port 22.

The skirt 38 of the concealment member 34 has an outer surface 60 that is spaced from the inner surface 30 of the sidewall 14 of the housing 12, although relative sliding contact may be provided between those surfaces. Where there is spacing between the surfaces 30 and 60, this most preferably applies throughout the extent of movement of the concealment member 34 longitudinally within the housing 12. The inner surface 30 of the sidewall 14 of the housing 12 preferably is of substantially uniform circular cross-section. The outer surface 60 of the skirt 38 of the concealment member 34 may be of substantially uniform circular cross-section although, as shown, it preferably has a slight taper so as to decrease in cross-section towards the end at which the transverse wall 48 of the concealment member 34 is provided. The slight taper may be such as to provide a half-cone angle of from about two to about six degrees. The inner surface of the skirt 38 of the concealment member 34, when the indicator member 26 is concealed or obscured, is preferably spaced from the outer peripheral surface 62 of the indicator member 26. This avoids contact between the skirt 38 of the concealment member 34 and the indicator member 26, and thereby obviates friction that could resist movement of the concealment member 34 relative to the indicator member 26. The skirt 38 of the concealment member 34 and the indicator member 26 each may be of uniform wall thickness along its respective axial extent, while they may be of similar or substantially the same wall thickness.

Figure 47:
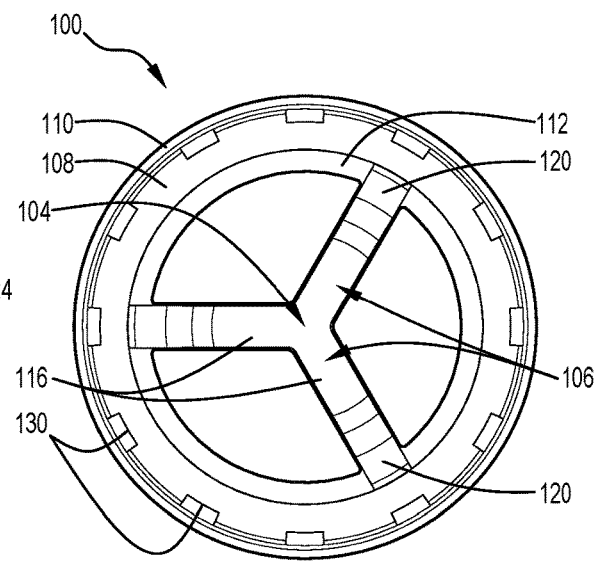
Figure 48:
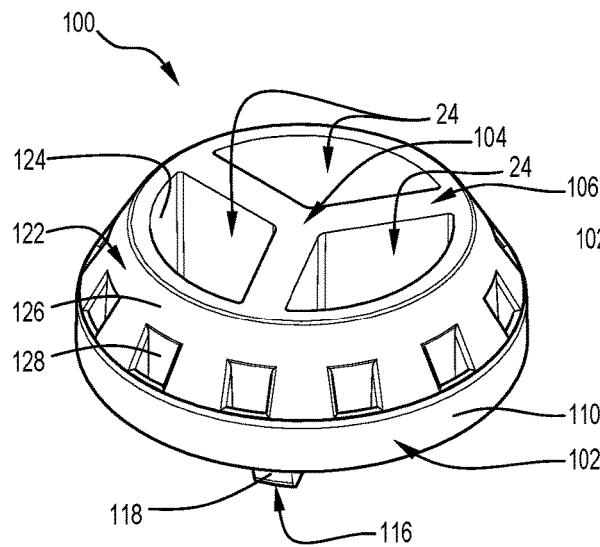
FIGS. 48 and 49 show a top and a bottom perspective view, respectively, of the fitting member of FIGS. 46 and 47, again on an enlarged scale.
Figure 49:
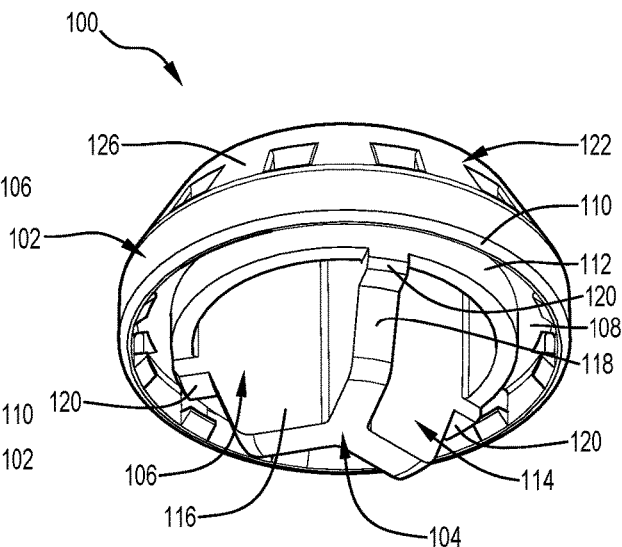

At the outlet end 18 of device 10, the housing 12 has a fitting member 100 through which the outlet ports 24 extend and open exteriorly from device 10. The fitting member 100 preferably is separable from the sidewall 14 of the housing 12. In the arrangement shown in FIGS. 2 to 15 and 46 to 49, the fitting member 100 has a rim 102, a hub 104 disposed within the rim 102 and circumferentially spaced connectors 106 by which the rim 102 is connected to the hub 104. As shown, a respective port 24 is defined between the rim 102 and the hub 104 and between successive pairs of the circumferentially spaced connectors 106. The rim 102 has an annular wall portion 108 (best seen in FIG. 47) that, with the fitting member 100 mounted on the second end 18 of the housing 12, abuts against or is closely adjacent to an end surface of the second end 18 of the housing 12, with the connectors 106 extending to the hub 104 from an inner periphery of the annular wall portion 108. The rim 102 also has an annular, outer skirt portion 110 extending around and from the outer periphery of the annular wall portion 108 such that, with the fitting member mounted on the second end 18 of the housing 12, the skirt portion 110 fits securely onto an end margin of the outer surface of the housing 12. Also, around the inner periphery of wall portion 108, the rim 102 has a second, inner skirt portion 112, best seen in FIGS. 47 and 49, that is substantially parallel with and spaced radially from skirt portion 110 and that engages the inner surface 30 of housing 12 when fitting member 100 is mounted on the second end 18 of housing 12. From the hub 104, fitting member 100 has an axially extended engagement portion 114 such that, with fitting member 100 so mounted on the housing 12, the engagement portion 114 projects within the second end 18 of housing 12, but is spaced from the inner surface 30 of the housing 12. The engagement portion 114 extends, beyond a respective free edge of each of the skirt portions 110 and 112. That is, the engagement portion 114 preferably has an axial extent or length from the wall portion 108 of the rim 102 that exceeds an axial extent or width of each skirt portion 110 and 112 from the wall portion 108. The axial extent of the engagement portion 114 may be such that the engagement portion 114 may extend beyond the free edge of skirt portion 110 and 112 by 1.5 to 4 times a spacing of the free edge of the skirt portions 110,112 from the wall portion 108 sufficient to enable the skirt portions 110,112 to grip the housing 12 for retaining fitting member 100 in relation to the housing 12. As a consequence, the axial extent or length of the engagement portion 114 able to project into the housing 12 is such that a number of beneficial arrangements are enabled.

The engagement portion 114 is preferably of a tri-star or three arm shape in transverse cross-sections, and is formed by extensions 116 of hub 104 and each connector 106. As seen most clearly from FIG. 49, each extension 116 is in the form of a fin and has a laterally outer side edge 118 that is shaped to define a step 120 that is spaced away from wall portion 108 of the rim 102, beyond the free edge of each skirt portion 110, 112 of the rim 102. Also, from step 120 to the free end of engagement portion 114 remote from the wall portion 108, the side edge 118 of each extension 116 is inclined so that engagement portion 114 is tapered so as to decrease in transverse cross-sections in a direction that is towards the free end of engagement portion 114, and that is away from the wall portion 108 of the rim 102.

The preferred coil spring comprising biasing member 36 is preferably positioned co-axially within housing 12 and with respect to transverse wall 48 of concealment member 34 and the engagement portion 114 of fitting member 100. One end of biasing member 36 bears against, and may be attached to, wall 48. Also, the tapered end portion of engagement portion 114 is received within and securely engages the other end of biasing member 36 to thereby hold the biasing member 36 under compression. The taper of the end portion of engagement portion 114, relative to the end portion of biasing member 36 in which engagement portion 114 is received, may be such that the end of the biasing member 36 is securely held in spaced relationship to steps 120, or it may be such the end of biasing member 36 bears against the steps 120. In either case the arrangement is such that the end of biasing member 36 is securely held to minimise or prevent biasing member 36 from being able to vibrate, and thereby result in a distracting sound. Additionally, the arrangement is such that the extent to which biasing member 36 can compress, as the concealment member 34 is being caused to move towards the second end 18 of housing 12 to expose indicator member 26, the biasing member 36 is prevented from being compressed to an extent that it can limit or prevent a required flow of gas through the housing 12.

Figure 43:
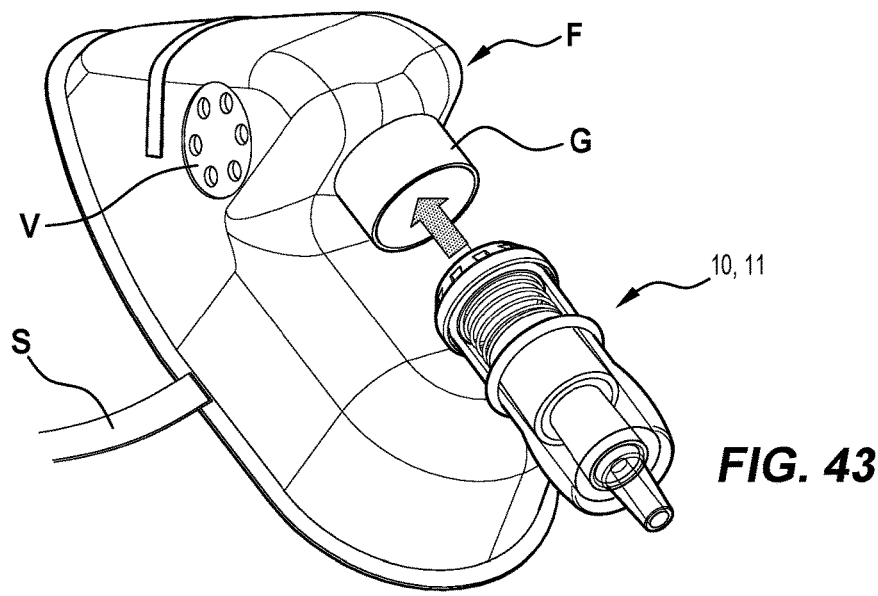
FIGS. 43 to 45 show successive stages in fitting of a device according to the invention to a facemask.
Figure 44:
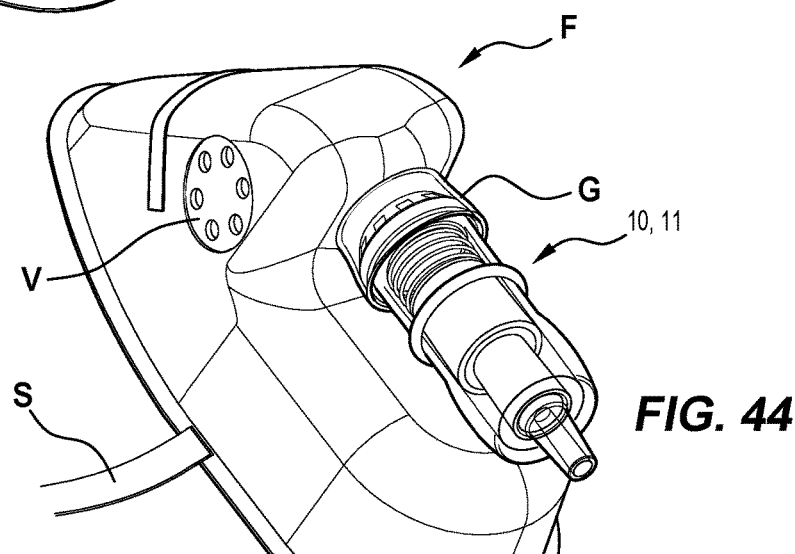
Figure 45:
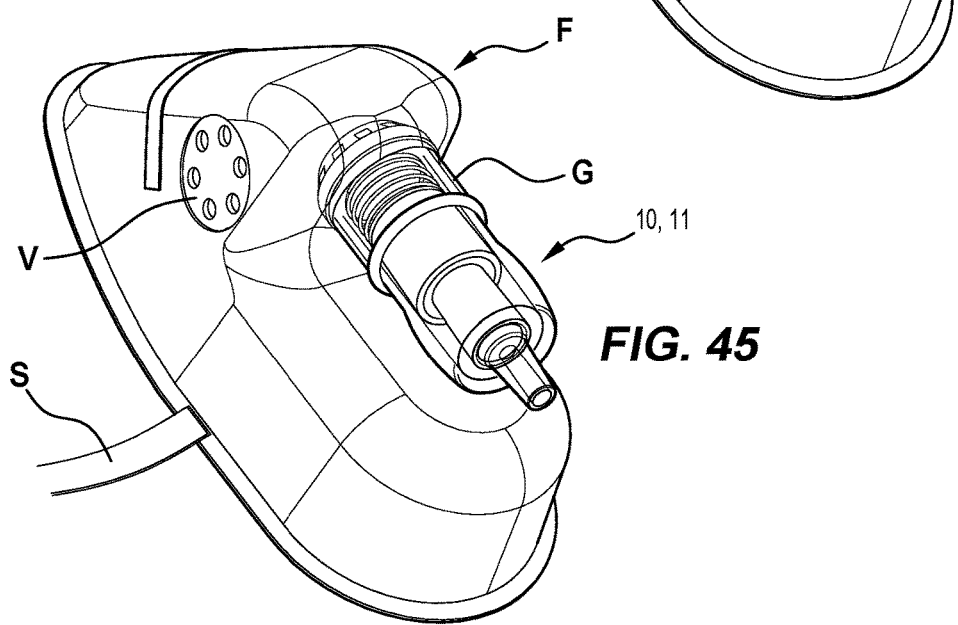
Figure 46:
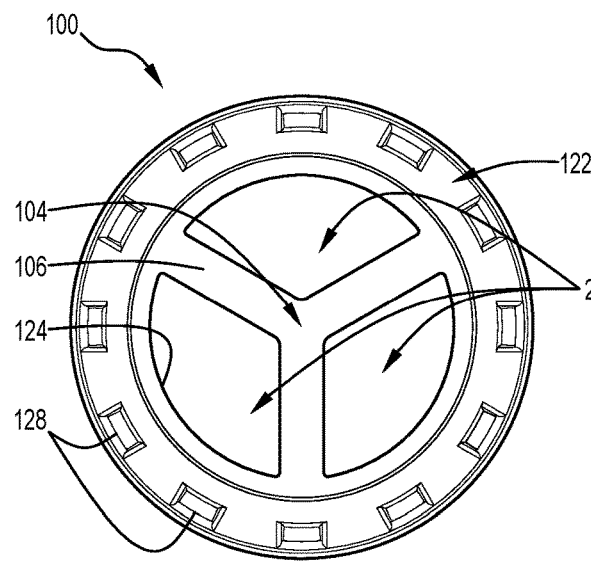
FIGS. 46 and 47 show on an enlarged scale a top and bottom plan view, respectively, of a fitting member for a device according to the invention.

The extensions 116 also have a portion 122 that extends in the opposite direction to engagement portion 114, within the thickness of wall portion 108 of rim 102. Around the portion 122 the rim 102 has an inner peripheral surface 124 that is a continuation of the outer surface of skirt 112, and a frusto-conical outer surface 126 that tapers to decrease in cross-sections in a direction away from engagement portion 114. As can be appreciated from FIGS. 43 to 45, showing the progressive fitting of a device 10 (or similarly a device 11—see FIGS. 21 to 24) to a facemask F, the taper of surface 126 facilitates insertion of the second end 18 of the device 10 into the gas inlet G of the facemask F. As shown, the portion 122 of extensions 116 may include a circumferential array of axially extending apertures 128 through rim 102. However, those apertures 128 are simply a manufacturing expedient to enable fitting member 100 as produced by moulding to include inward projections 130 spaced around the free edge of skirt portion 110, with projections 130 facilitating securement of fitting member 100 by providing a snap fit over bead 132 provided around the second end 18 of housing 12. However, the portion 122 also provides an extension of device 10 beyond the second end 18 of housing 12 that results in the outlet port 24 being at an elevated position above the upper end of gas inlet G of a facemask F, thereby providing a protective physical boundary to passive drainage of any expectorated secretions (blood, mucous or vomitus) into the device 10, potentially affecting its function. As a further safety measure against such secretions, a perforated mesh (not shown) may cover over the distal outflow tract of the fitting member 100, to provide multiple holes or perforations, such as tapered from an inner to an outer surface that while not adding any significant resistance to gas flow could restrict ingress of such fluids by surface tension or by localised acceleration of gas flow that causes the fluid to be ejected from the mesh.

Figure 13:
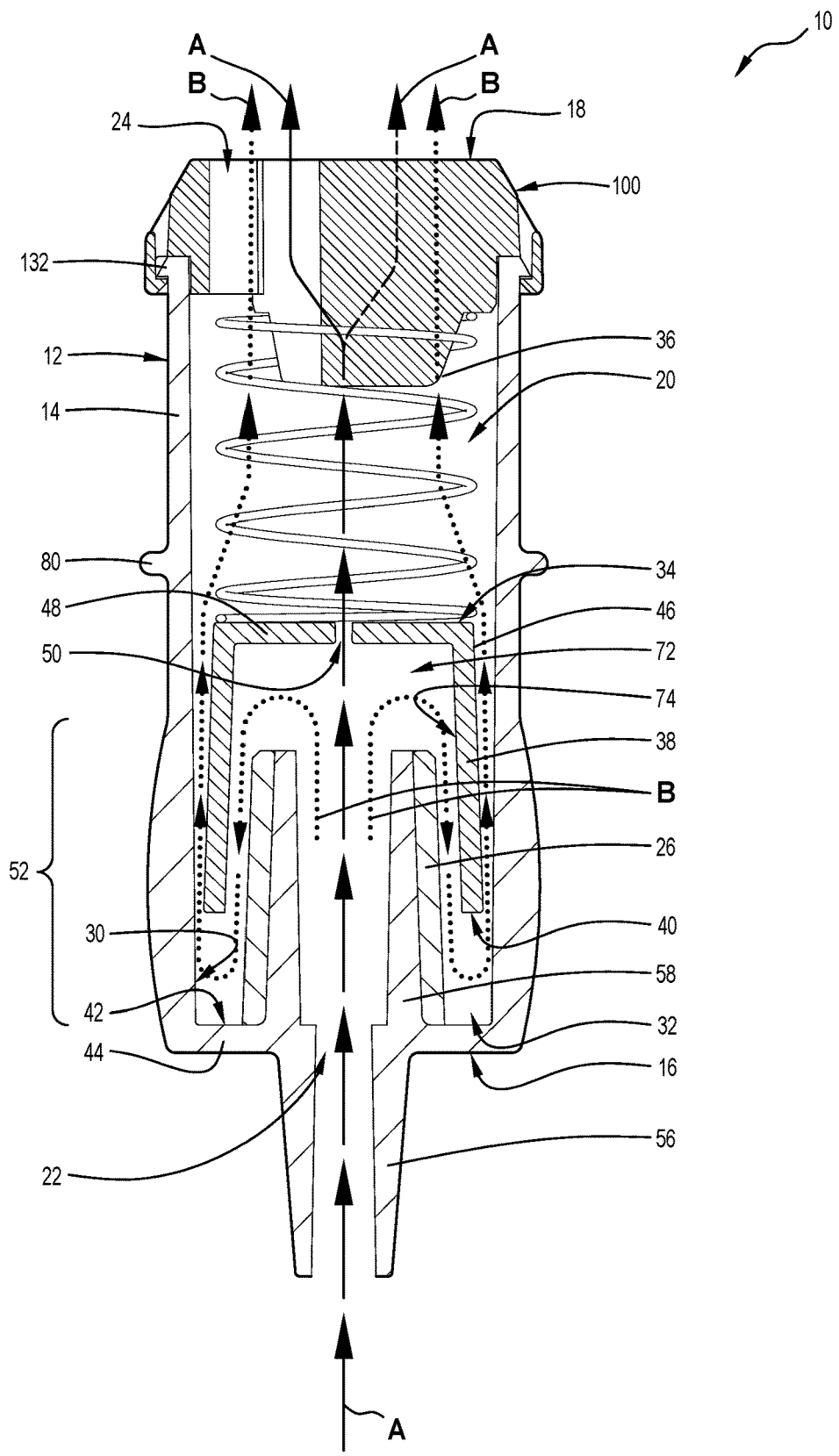
FIG. 13 is a schematic representation of the device of FIG. 2, illustrated in operation in accordance with the condition shown in FIG. 7.
Figure 25:
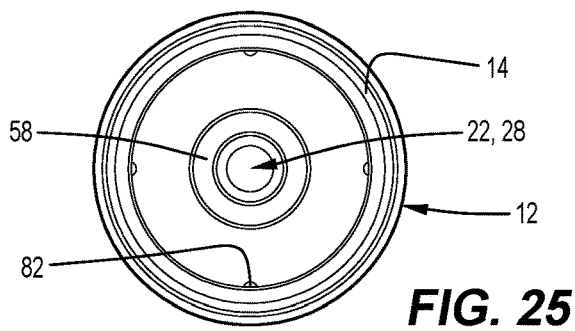
FIGS. 25 to 28 show an end elevation, a side elevation, a perspective view and a section view taken on line Z-Z of FIG. 26, respectively of a component suitable for the device of FIGS. 2 to 20, or the device of FIGS. 21 to 24.
Figure 26:
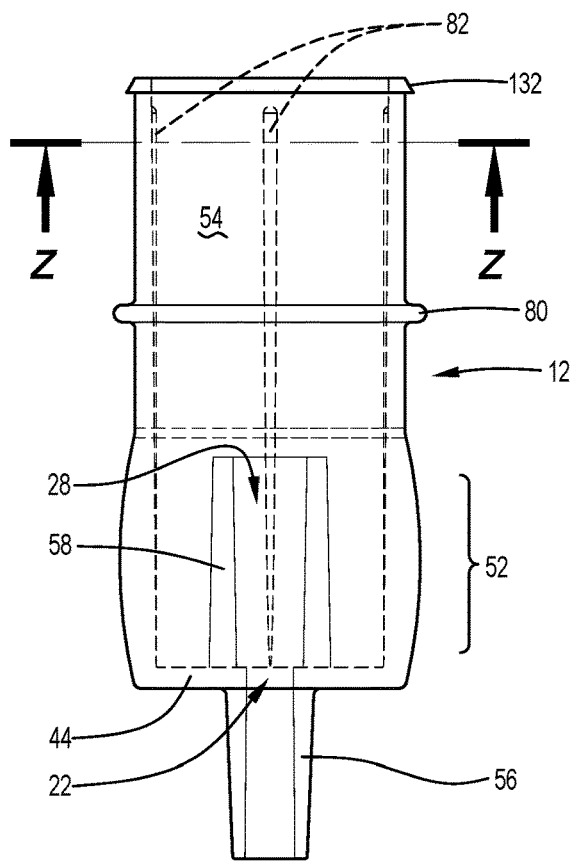
Figure 27:
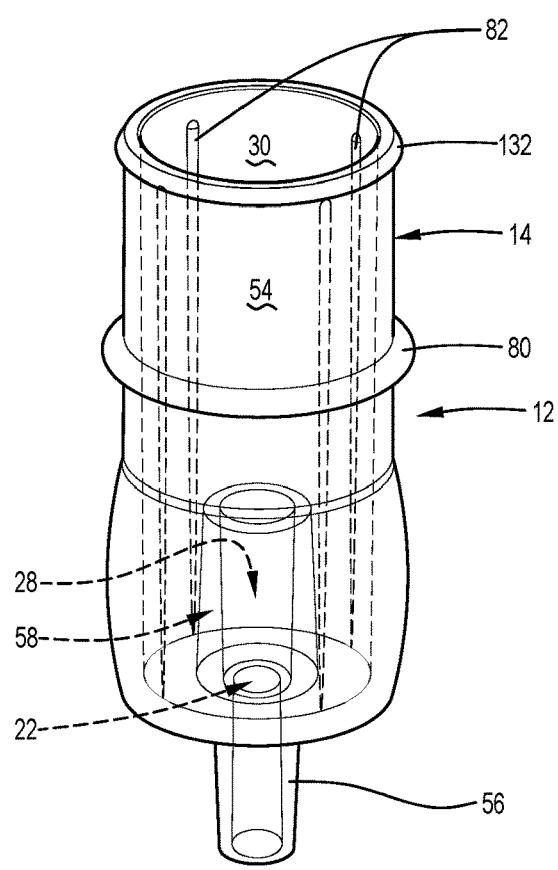
Figure 28:
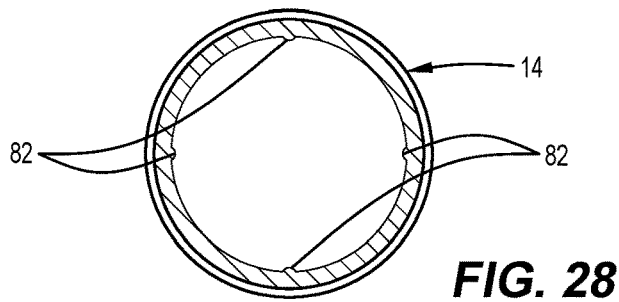

In use of the device 10, required gas, such as oxygen or oxygen-enriched air, is supplied through device 10. In the arrangement of FIG. 1, for example, the gas is supplied through conduit C so as to flow through spigot 56 and then through inlet port 22 and bore 28. From bore 28, the gas flows into a sub-chamber 72 (see, for example, FIGS. 11 & 13) defined within concealment member 34, indicator member 26 and end wall 44 of housing 12, before flowing through opening 50 of transverse wall 48, of concealment member 34, to pass into chamber 20, before exiting through outlet port 24 into facemask F. The gas received into facemask F then can be inhaled by patient P, and is supplied at a rate appropriate for the patient's P needs. Balancing the pressure at which the gas is supplied to conduit C, and the resistance to the flow of gas through conduit C and through device 10, enables compliance with the patient's P needs. Within device 10, the resistance to flow is determined by the size of opening 50 relative to the area of transverse wall 48, of concealment member 34, and the compressibility of the spring comprising biasing means 36. Opening 50 is such as to resist gas flow from sub-chamber 72 to chamber 20, causing a generation of gas pressure against transverse wall 48 that, supplemented by pressure against the tapered inner surface 74 of skirt 38, acts to oppose the bias of biasing member 36 and tends to move concealment member 34 away from the inlet end 16 of housing 12, towards the outlet end 18. The resistance to gas flow provided by opening 50 is designed to result in the pressure in sub-chamber 72 increasing to a level at which such movement of concealment member 34 occurs, with consequential breaking of the sealing engagement between the end 40 of skirt 38 of concealment member 34 and the annular abutment surface 42 defined by housing 12. The gas flow through opening 50 is somewhat centralised in a gas stream along an axial line through device 10, as depicted in FIG. 13 by solid-line arrows A-A. However, with that break in sealing engagement between end 40 of skirt 38 and abutment surface 42, a second gas stream commences, with this being radial, outwardly between end 40 and abutment surface 42, and then as an annular curtain of gas passing to outlet port 24 between the inner surface 30 of sidewall 14 of housing 12 and the outer surface 60 of skirt 38 of concealment member 34. In FIG. 13, the dotted-line arrows B-B depict the second, annular curtain gas stream.

As illustrated in FIG. 13, the pressure of gas within the sub-chamber 72 of the concealment member 34, against transverse wall 48, acts against the bias of biasing means 36 and enables initiation of movement of concealment member 34 that permits generation of the second gas stream depicted by arrows B-B. This results in a reduction of pressure within concealment member 34, although the reduced pressure against wall 48 is supplemented by gas pressure against the annular area of end 40 of skirt 38, as well as a reduced pressure prevailing over the tapered outer surface 60 of skirt 38 relative to the pressure over the tapered inner surface 74 of skirt 38. The overall balance achieved with application of a gas supply pressure within a typical range is such that the concealment member 34 is moved against the biasing member 36 a distance exposing a sufficient axial extent of indicator member 26 whereby indicator member 26 is visible through the laterally adjacent viewing window portion 52 of housing 12. The arrangement is such that concealment member 34 typically is moved beyond the position shown in FIG. 13, such as to a position able to be seen in each of FIGS. 2, 7 and 15, so that the external surface 62 of indicator member 26 is exposed and able to be viewed through the laterally adjacent window portion 52 of housing 12. For this, the spacing within chamber 20 between the outlet end 18 of housing 12 and the nearer end of indicator member 26 is able to accommodate concealment member 34 and the compressed coils of the spring comprising biasing member 36. However, with termination of or an interruption to gas flow through device 10, the bias provided by biasing member 36 acts to return the concealment member to its position in which it conceals or obscures indicator member 26 from view.

The indicator member 26 preferably is made of or coated with a material that maximises its visibility. Thus, the material may have a strong, vibrant colour, or it may be iridescent, fluorescent or highly reflective, so as to draw the eye E (see FIG. 38) of a person charged with observing the patient P from time to time to ensure a required supply of gas is being maintained. In addition to such materials and effects, the outer surface 62 of indicator member 26 may be marked, textured or patterned as shown in FIGS. 16 to 18. Thus, FIG. 16 shows indicator member 26 as provided graduated markings 78 facilitating fine-tuning and observance of maintenance of the flow of gas through device 10, such as by appropriate adjustment of a source of gas supply. FIG. 17 shows an indicator member 26 having an outer surface 62 that is textured to maximize its exposure being observed, even in low lighting conditions. FIG. 18 shows an indicator member 26 that is patterned in a checkerboard to provide a plurality of areas differing in colour, texture or both colour and texture.

Reverting to FIG. 3, which shows an example of a facemask F with which the device 10 is usable. The facemask F has a main body M, a gas inlet G, ventilation apertures V and, around the edge of body M, openings O by which, as shown in FIG. 1, the facemask F can be retained in position on the face of a patient P by straps S. The gas inlet G is of tubular form and the outlet end 18 of device 10 is a neat sliding fit in inlet G. As is shown, device 10 preferably has a peripheral bead 80 around the exterior of housing 12 that ensures the outlet end 18 of device 10 is not inserted too far into gas inlet G of facemask F.

In the preferred form of device 10 depicted in FIGS. 8, 9, 11 and 13, ease of assembly of device 10 readily can be appreciated. In this preferred form, indicator member 26 may first be inserted into the outlet end 18 of housing 12 and fitted onto and secured in relation to the hub 58 provided as an extension of spigot 56. Concealment member 34 may then be positioned over indicator member 26 to position the inlet end 40 of skirt 38 of concealment member 34 against the abutment surface 42. The coil spring comprising biasing member 36 may then be positioned within the outlet end 18 of housing 12 and compressed down onto transverse wall 48 of concealment member 34 by application of fitting member 100 onto the outlet end 18 of housing 12.

FIGS. 19 and 20 show device 10 in a different arrangement to that of FIG. 1. In FIGS. 19 and 20, the device 10 is installed in a conduit line that has an inlet conduit length C1 connected onto spigot 56 in the manner shown for conduit C of FIG. 1. However, device 10 is provided with a fitting member 100 that has an integral spigot 76 that projects axially away from housing 12. The spigot 76 has a second conduit length C2 connected, thereto with gas passing through device 10 being received into conduit length C2 by which the gas is passed to a required location. The required location may be, for example, a facemask, bag valve mask or endotracheal tube, etc.

FIGS. 21 to 24 illustrate an alternative form of gas flow indicator device 11 according to the invention. The structure of device 11 generally will be understood from the description of device 10 of the preceding Figures, and corresponding components have the same reference numeral, plus 1 (with the exception of fitting member 100, and its component parts/features, which bear the same reference numerals). FIGS. 21 to 24 generally will be understood from the description of device 10 of the preceding Figures, and description of device 11 therefore will be limited to principle matters of difference between device 10 and device 11. A principle feature of difference resides in the device 11 having a biasing member 37 preferably comprising a coil spring that is located within the concealment member 35. The biasing member 37 is in tension so that the inlet end 41 of skirt 39 of the concealment member 35 is pulled into sealing engagement with an annular abutment surface 43 defined by housing 13 at or adjacent to an end wall 45 of the housing 13 at the inlet end 17 of the housing 13. The biasing member 37 has one of opposite ends engaged with end wall 45 of housing 13, around the inlet port 23. The other of the opposite ends of the biasing member 37 is secured to an annular boss 77 that is provided on the transverse wall 49 of concealment member 35, within sub-chamber 73, and that defines the opening 51 in transverse wall 49. Thus, as can be appreciated from a comparison of FIGS. 22 and 23, the movement of concealment member 35 to expose the indicator member 27 increases tension in the biasing member 37. Termination or interruption of gas flow through device 11 thus results the bias provided by biasing member 37 returning concealment member 35 to its position in which it conceals or obscures indicator member 27 and prevents indicator member 27 from being viewed through window portion 53 of housing 13.

A further important difference in the device 11 of FIGS. 21 to 24 is that the engagement portion 114 of fitting member 100 does not directly engage the biasing member 37, due to the biasing member 37 acting in tension and being located within the concealment member 35. Thus, the engagement portion 114 of fitting member 100 does not secure an end on biasing member 37 so as to preclude vibrations, although vibrations are able to be at least minimised by the engagement between the biasing member 37 and the concealment member 35. However, the engagement portion 114, of fitting member 100, is able to interact with biasing member 37 as a consequence of being able to set a stop for concealment member 35 that limits the extent of movement of concealment member 35 towards the second end 19 of housing 13, thereby setting a limit on the extent to which biasing member 37 can be tensioned.

FIGS. 25 to 28 show a housing 12 suitable for the device 10 shown in FIGS. 2 to 20, but with a modification that also can be adopted in the housing 13 of the device 11 of FIGS. 21 to 24. The modification is in the provision, along the inner surface 30 of the sidewall 14 of housing 12, of a number of longitudinally extending, circumferentially spaced ribs 82. In the arrangement shown, there are four ribs 82, although there may only be three (or less) or there may be more than four ribs 82. The ribs 82 preferably are uniformly spaced from each other around inner surface 30 of housing 12, while the cross section of each rib 82 is such that it substantially bridges the spacing between the inner surface 30 of housing 12 and the outer surface 60 of skirt 38 of concealment member 34 without impeding movement of the concealment member 34 with or against the bias of the biasing member 36. Despite this, the ribs 82 do serve to centralize the concealment member 34 during such movement and when stationary. Ribs 82 also serve to obviate noise or vibrations due to the concealment member 34 rattling or oscillating laterally within housing 12 during use of device 10.

It is to be appreciated that while ribs 82 are illustrated in FIGS. 25 to 28, other alternative centralizing formations could be provided. For example, inner surface 30 of sidewall 14 of housing 12 could have formed thereon a plurality of small protrusions that are spaced over, both along and around, the inner surface 30 of housing 12. In a further alternative arrangement, the centralizing and/or noise reduction formations, such as ribs or protrusions could be provided over the outer surface 60 of skirt 38 of concealment member 34, rather than over inner surface 30 of the sidewall 14 of housing 12.

FIGS. 29 to 32 illustrate alternative construction detail by which indicator member 26 may be secured concentrically on the hub 58 comprising a continuation of spigot 56 of device 10 of FIGS. 2 to 20. The same alternatives apply to the securement of the indicator member 27 on the hub 59 in the device 11 of FIGS. 21 to 24. In FIG. 29, the indicator member 26 is a neat fit on hub 58, such as to provide a strong friction fit or with securement enhanced by a film providing adhesive bonding. FIG. 30 shows an arrangement in which concealment member 26 is spaced slightly from hub 58 but is secured by an adhesive bonding layer 84 between the opposed surfaces of member 26 and hub 58. In the alternative of FIG. 31, more clearly illustrated by the enlarged detail of FIG. 32, a fusible fin 86 is provided around the end of indicator member 26 opposed to end wall 44 of housing 12 and, when the fin 86 is heated by any suitable arrangement, the fin 86 melts to bond that end of member 26 to wall 44.

Further alternatives for securing indicator member 26 on hub 58 of device 10, with similar possible for securing member 27 on hub 59 of device 11, are shown in FIGS. 33 and 35, with FIGS. 34 and 36 providing respective enlarge detail. In the arrangement of FIGS. 33 and 34, the indicator member 26 is shown as having an in-turned flange 88 around the end of indicator member 26 remote from end wall 44 of housing 12. The flange 88 overlaps the adjacent end of hub 58, with a fin 90 on flange 88 bearing against that adjacent end of hub 58. Heating of the fin 90 by any suitable arrangement enables the fin 90 to melt, with indicator member 26 then able to move more firmly onto hub 58 and be secured by flange 88 being fusion bonded to the adjacent end of hub 58. In the case of FIGS. 35 and 36, there is provided a mechanical securement of indicator member 26 onto hub 58. For this, the end of indicator member 26 opposed to end wall 44 of housing 12 has an array of circumferentially spaced, axially projecting hooked fingers 92. As indicator member 26 is moved onto hub 58, each finger 92 is forced to elastically flex so as to enter a respective aligned opening 94 through end wall 44 of housing 12. When indicator member 26 is fully received onto hub 58, each finger 92 is able to elastically recover, to locate its out-turned end against the outer surface of end wall 44 and thereby lock indicator member 26 on hub 58.

Figure 37:
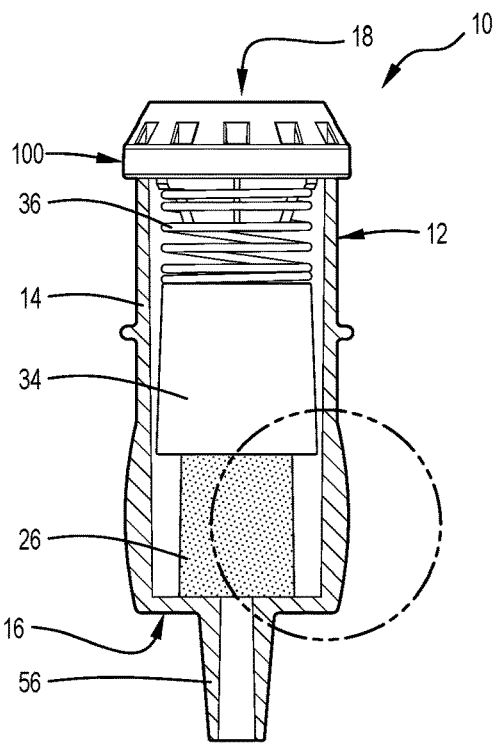
FIG. 37 is similar to FIG. 15, but highlights an encircled region of the device.
Figure 38:
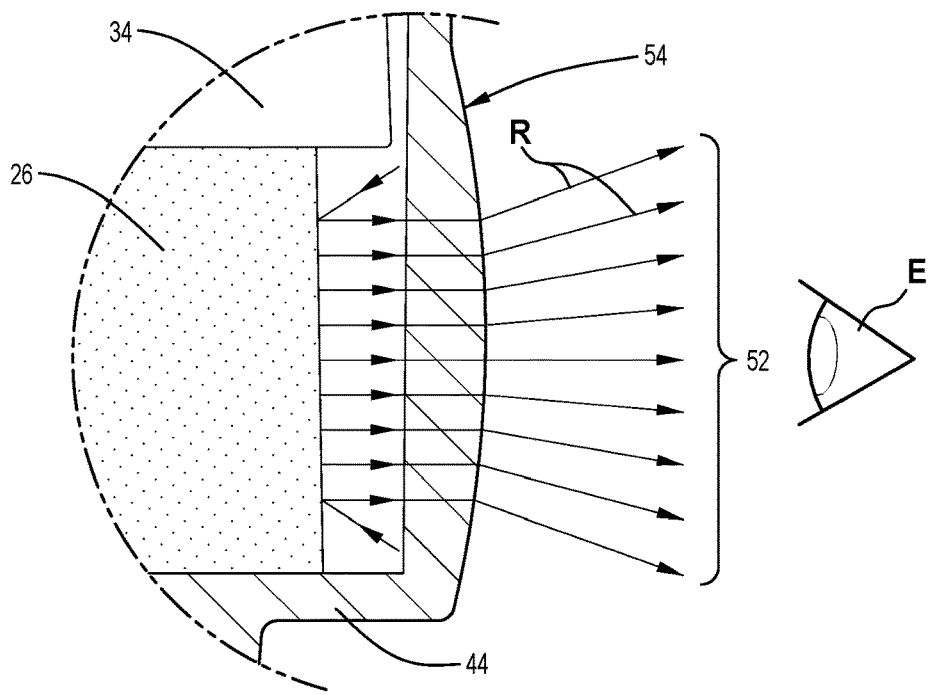
FIG. 38 illustrates performance with the encircled region of FIG. 37.

FIG. 37 and, in particular, the enlarged detail of FIG. 38, elaborates on the description above in relation to the viewing window portion 52 of the housing 12 of device 10 shown in FIGS. 2 to 20, with the same being applicable to the corresponding features of device 11 of FIGS. 21 to 24. As can be recognized from the schematic view of FIG. 38, in particular, the longitudinally arcuate form of the outer surface 54 of housing 12, within the window portion 52, enables window portion 52 to function as a magnifying lens. The effect is such that light rays R shown as issuing out from indicator member 26 diverge out from window portion 52. While the eye E of an observer is depicted as close to window portion 52, the lens effect is such as to permit viewing of indicator member 26 from a considerable distance, as indicator member 26 is seen as enlarged relative to its actual size and also to be viewed over a wider viewing angle. These factors, combined with the colour and/or other preferred highlighting features of indicator member 26, facilitate indicator member 26 being readily viewed when it is exposed by movement of concealment member 34, as a consequence of a desired or required flow of gas through the device 10.

Figure 39:
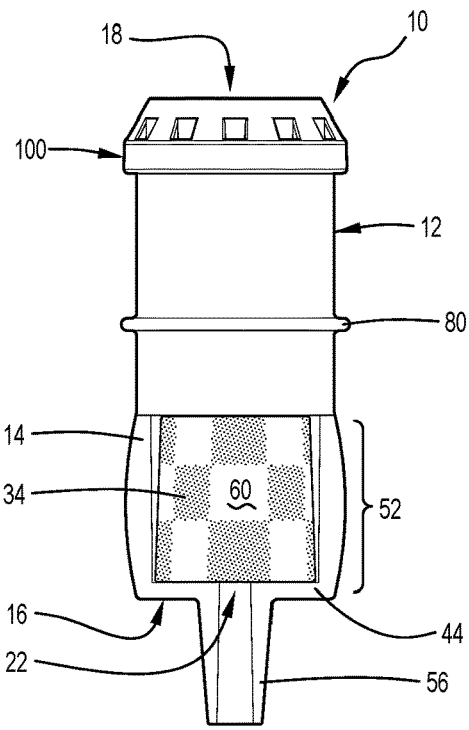
FIGS. 39 to 42 illustrate different detail for components of the device of FIG. 2, but also applicable to the device of FIGS. 21 to 24.
Figure 40:
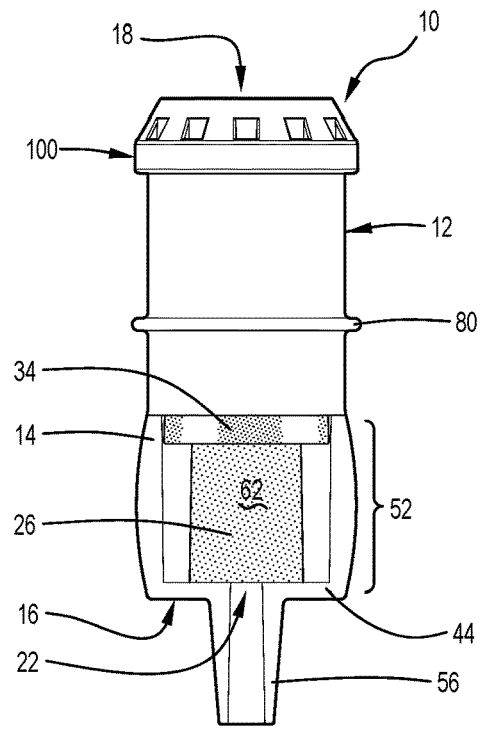
Figure 41:
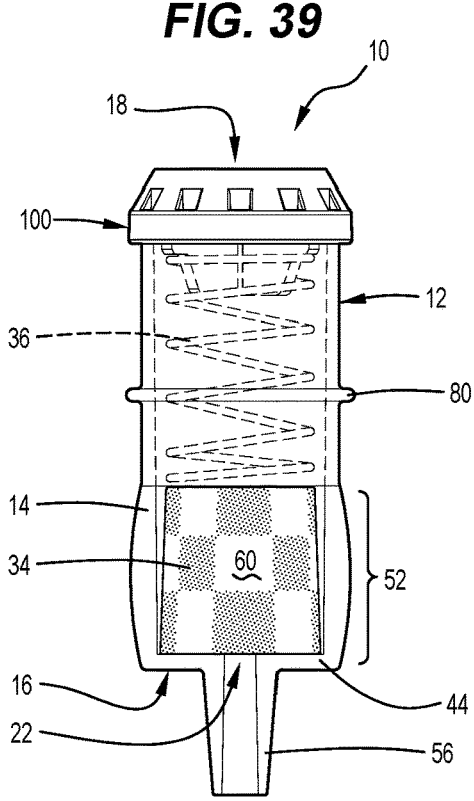
Figure 42:
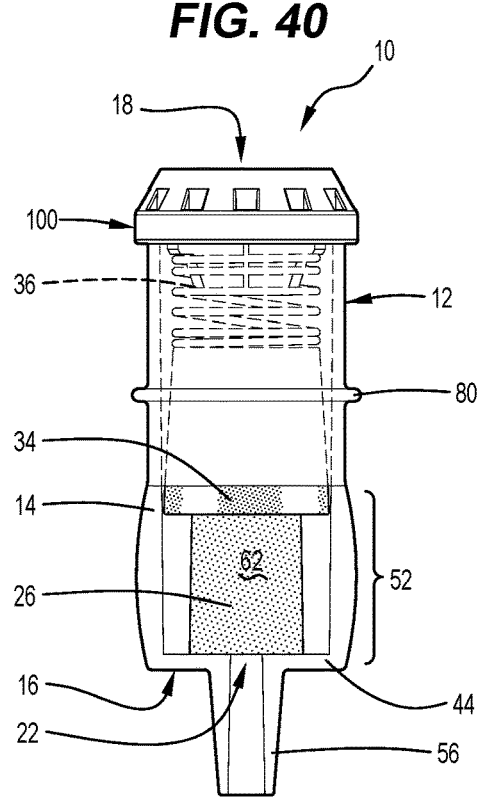

FIGS. 39 to 42 illustrate further variants possible to assist with recognition of the operating condition of device 10 of FIGS. 2 to 20, with the same being applicable to device 11 of FIGS. 21 to 24. FIGS. 39 and 41 show the same condition for device 10, with the indicator member (not visible) in this instance being concealed by the concealment member 34, although FIG. 41 shows internal structure consistent with this. FIGS. 40 and 42 also are the same condition for device 10, but with the indicator member 26 exposed as a consequence of movement of the concealment member 34 in response to a required gas flow, although FIG. 42 shows internal structure consistent with this. The variant depicted in FIGS. 39 to 42 is the provision of patterning, colouring and texture differences adopted for the external surface 60 of the skirt 38 of concealment member 34, relative to the outer surface 62 of the indicator member 26. The contrast between surfaces 60 and 62 is such that a viewer is even more readily able to distinguish the surface 60, seen through the window portion 52 when concealment member 34 is concealing the indicator member 26, from the surface 62 seen when indicator member 26 is exposed by movement of concealment member 34 as a consequence of a required flow of gas through device 10. Thus, checking that gas is flowing, as required can be even more reliably and readily confirmed. Also, as is evident from FIGS. 39 to 42, the length of the housing 12 between the transparent window portion 52 and the second end 18 may be opaque (or coated with an opaque material or coating, etc.) and of any suitable colour, thereby serving to maximise the visual contrast between the respective conditions in which the indicator member 26 is concealed or exposed. Also, where device 10 is to be one of a series as discussed later herein, that opaque length of the housing 12 may carry indicia that distinguishes that device 10 from others of the series.

At, or adjacent to the inlet end 16 or 17 of the respective devices 10 or 11, there may be at least one opening enabling ambient air to be drawn through the respective chamber 20 or 21, to mix with gas such as oxygen or oxygen-enriched air being supplied to a patient P. The opening may be in the end wall 44 or 45, such as shown by hole 96 in device 10 of FIGS. 3, 8 and 9. Alternatively the, or each, opening (not shown) may be in the side wall 14 or 15 of respective device 10 or 11, closely adjacent to the end wall 44 or 45. Where the opening or openings is/are in end wall 44 or 45 (e.g. 96), its/their position is such that it/they is/are fully covered by the nearer end 40 or 41 of skirt 38 or 39 of the concealment member 34 or 35 when that end 40 or 41 of the skirt 38 or 29 is in sealing engagement with the end wall 44 or 45. In any event, ambient air is precluded from being drawn into the chamber 20 or 21, through the opening or openings (e.g. 96), until the seal between end 40 or 41 of skirt 38 or 39, of concealment member 34 or 35, is broken by the flow rate of the supply gas increasing to generate the sufficient pressure to cause the concealment member 34 or 35 to move against the action of the biasing member 36 or 37, to enable the secondary flow of the supplied gas around the exterior of the concealment member 34 or 35. It is the secondary flow, in passing across the at least one opening (e.g. 96) that draws in the ambient air, by creating a Venturi effect.

As will be appreciated, the gas flow indicator device of the invention enables enhanced ease of observation of a condition, namely exposure of the indicator member, confirming required supply of gas to a patient. With full exposure of the indicator member preferably also confirming that a desired or minimum gas flow rate, such as 6 L/min, has been achieved and is being maintained. The device has components that enable low cost production, readily assembled and provide reliable operation. Also, the device is such that it can be provided in a number of alternative forms each suited to providing a respective required gas flow rate. Thus, for a given standardised biasing member, it is possible to vary performance by selecting from a series of devices that differ in the size of the opening of respective concealment members and, hence, the gas flow rate that is required to move the concealment member to expose the respective indicator member. Alternatively, a series of devices may have a standardised such opening in the respective concealment members, but differ in the strength of the biasing action of the respective biasing members. Thus, in each case, a respective gas flow rate is required for each device of the series in order to overcome the resistance to flow provided by the respective opening of the concealment member in order for the concealment member to move against the action of the biasing member. The different devices of such series can be readily differentiated by the colour or indicia provided on the outer surface of the skirt of each concealment member, or elsewhere on the device, such as on the housing. Of course, the device also may be provided in a single standardised form, with the gas flow rate at any time within a suitable range of flow rates being apparent from the extent of exposure of the indicator member.

All components of the device of the invention are able to be of non-ferrous materials, indeed none of the components need be metallic, making the device suitable for use with a facemask supplying gas to a patient while the patient is undergoing an MRI or other procedure precluding metals. Also, the device can be used in any orientation, in contrast, for example, to apparatus utilising a ball valve type of flow mechanism. Also, the construction of the device is such as to enable continuance of gas supply by minimising the risk of the concealment member becoming snagged, while enabling ongoing gas supply even if the concealment member does become snagged.

While this invention has been described in connection with specific embodiments thereof, it will be understood that it is capable of further modification(s). The present invention is intended to cover any variations, uses or adaptations of the invention following in general, the principles of the invention and including such departures from the present disclosure as come within known or customary practice within the art to which the invention pertains and as may be applied to the essential features hereinbefore set forth. As an example applicable to the device 10 of any of FIGS. 2 to 20, the concealment member 34 may have a rim formed around the periphery of transverse wall 48 that serves to locate the adjacent end coils of the spring comprising biasing member 36 or, around the opening 50 in transverse wall 48, the concealment member 34 may define an engagement portion projecting so as to locate in those end coils. In each case, the arrangement may be such as to secure the biasing member against vibration so as to avoid resultant noise.

As the present invention may be embodied in several forms without departing from the spirit of the essential characteristics of the invention, it should be understood that the above described embodiments are not to limit the present invention unless otherwise specified, but rather should be construed broadly within the spirit and scope of the invention as defined in the attached claims. Various modifications and equivalent arrangements are intended to be included within the spirit and scope of the invention. Therefore, the specific embodiments are to be understood to be illustrative of the many ways in which the principles of the present invention may be practiced.

Where the terms "comprise", "comprises", "comprised" or "comprising" are used in this specification, they are to be interpreted as specifying the presence of the stated features, integers, steps or components referred to, but not to preclude the presence or addition of one or more other features, integers, steps, components to be grouped therewith.

The invention claimed is:

1. A gas flow indicator device including:
   (a) an elongate housing that has a peripheral sidewall that extends between first and second opposite ends and that defines a gas flow chamber through which gas is able to flow from an inlet port at a first end to an outlet port at a second end;
   (b) a gas flow indicator member within the chamber that extends from adjacent to the first end of the housing over part of the length of the chamber towards the second end, with the indicator member being of annular form such that gas flowing through the chamber from the inlet port to the outlet port enters the chamber along a bore that extends through the indicator member and with the indicator member spaced from an inner surface of the sidewall of the housing to define, with that inner surface, an annular space that forms part of the chamber;
   (c) a concealment member that is movable from the first end of the housing in response to a sufficient pressure generated by gas flow from the inlet port to the outlet port, against the action of a biasing member acting to bias the concealment member to the first end, the concealment member having an annular peripheral skirt that, under the bias of the biasing member on the concealment member, is receivable into the annular space, such that one of opposite ends of the skirt is able to seal against an annular surface of the housing at or adjacent to an end wall of the housing at the first end of the housing, with the concealment member also including, at the other of the opposite end of the skirt, a transverse wall that defines an opening through which the flow of gas from the inlet port to the outlet port is able to pass, with the opening providing resistance to such flow;
   (d) with the arrangement such that the one of opposite ends of the skirt is able to be held in sealing engagement with the annular surface at or adjacent to the end wall of the housing whereby the indicator member is concealed or obscured from view, through a laterally adjacent viewing window portion of the housing, when there is no gas flow or a gas flow rate generating less than the sufficient pressure but such that, with increasing gas flow rate the sufficient pressure is achieved and the bias of the biasing member is thereby overcome to enable the concealment member to move towards the second end of the housing and expose the indicator member to view through the viewing window portion of the housing and provide a visual indication indicative of gas flow; and,
   (e) wherein the device further includes a fitting member mounted at the second end of the elongate housing that has a rim, a hub disposed within the rim and circumferentially spaced connectors by which the rim is connected to the hub, with a respective opening defined between the rim and the hub between successive pairs of the circumferentially spaced connectors; the rim has an annular wall portion that abuts against or is closely adjacent to an end surface of the second end of the housing, with the connectors extending to the hub from an inner periphery of the annular wall portion, and an annular skirt portion extending around and from the outer periphery of the annular wall portion such that, the skirt portion fits securely onto an end margin of the outer surface of the housing; the fitting member has an engagement portion that has an axial extent from the hub and connectors such that the engagement portion projects from the wall portion into the housing from the second end, and beyond a free edge of the skirt portion spaced from the wall portion, with the engagement portion spaced from the inner surface of the housing.

2. The gas flow indicator device of claim 1, wherein the axial extent of the engagement portion is such that the engagement portion extends beyond the free edge of the skirt portion by 1.5 to 4 times a spacing of the free edge of the skirt portion from the wall portion sufficient to enable the skirt portion to grip the housing for retaining the fitting member in relation to the housing.

3. The gas flow indicator device of claim 1, wherein the biasing member acts in compression, and the engagement portion of the fitting member engages an end of the biasing member that is remote from the concealment member.

4. The gas flow indicator device of claim 3, wherein the biasing member is a coil or helical spring, and the engagement portion engages with the end of the spring that is remote from the concealment member, with the engagement portion fitting within, and restricting movement of, the remote end of the spring.

5. The gas flow indicator device of claim 4, wherein the engagement portion limits, or substantially precludes, movement of the remote end of the spring laterally with respect to the inner surface of the housing, or longitudinally away from the concealment member, or both laterally with respect to the inner surface of the housing and longitudinally away from the concealment member.

6. The gas flow indicator device of claim 5, wherein the engagement portion engages the remote end on the spring at a location spaced from the wall portion of the rim of the fitting member, most preferably a location spaced from the wall portion beyond the free edge of the skirt portion of the rim.

7. The gas flow indicator device of claim 4, wherein the engagement portion has a tapered or frusto-conical form, and decreases in cross-section in a direction away from the wall portion of the rim, with a free end that is spaced from the wall portion and received within the remote end of the coil or helical spring, with the taper of the engagement portion relative to the diameter of the spring resulting in an interference fit between the remote end of the spring and a location intermediate of opposite ends of the engagement portion that limits the extent to which the engagement portion is able to be received within the spring, whereby the engagement portion provides an abutment that restricts movement of the spring.

8. The gas flow indicator device of claim 4, wherein the engagement portion is stepped intermediate of its ends, to provide a free end portion of lesser, preferably substantially uniform, cross section than a remainder portion nearer to the wall portion of the rim, with an annular abutment shoulder being defined at the step, whereby the free end portion of the engagement portion is able to be received, preferably as a neat fit, within the remote end of the spring to limit or substantially preclude lateral movement of that remote end, and such that the shoulder provides an abutment against which the remote end of the spring bears thereby to restrict or substantially preclude longitudinal movement of that remote end.

9. The gas flow indicator device of claim 1, wherein the fitting member has an end portion beyond the rim in a direction away from the engagement portion, with the end portion tapered to decrease in cross-sections in that direction away from the engagement portion to facilitate insertion of the device into a facemask to a position at which the outlet port is positioned at a height minimising the ingress of expectorated secretions; the outlet port optionally incorporating perforated mesh facilitating restriction of the ingress of expectorated secretions by surface tension forces or the pressure of gas flow from the device.

10. The gas flow indicator device of claim 1, wherein movement of the concealment member to expose the indicator member moves the one of opposite ends of the skirt of the concealment member from the annular surface at or adjacent to the end wall of the housing, such as thereby to enable a secondary gas flow to the outlet port that passes around the one of opposite ends of the skirt between the concealment member and the housing.

11. The gas flow indicator device of claim 1, wherein the biasing member acts in compression in biasing the concealment member to the first end of the housing, such as by the biasing member being compressed between, such as compressed by, the concealment member and the second end so as to provide the required bias in seeking to expand.

12. The gas flow indicator device of claim 1, wherein the biasing member acts in tension in biasing the concealment member to the first end of the housing, such as by the biasing member being within the concealment member, and tensioned by being expanded between, such as by being connected in relation to, each of the transverse wall of the concealment member and the first end of the housing so as to provide the bias in seeking to contract.

13. The gas flow indicator device of claim 1, wherein the biasing member comprises a coil spring.

14. The gas flow indicator device of claim 11, wherein the biasing member comprises a coil spring acting between the concealment member and the second end of the housing, and wherein compression of the spring can limit the extent to which the concealment member can move towards the second end of the housing simply as a consequence of the presence of the compressed spring.

15. The gas flow indicator device of claim 12, wherein the biasing member comprises a coil spring within the concealment member, with the arrangement such that the concealment member is able to move so as to contact the end wall at the second end of the housing, or such that contact of the concealment member with the second end of the housing is precluded by the spring reaching its elastic limit.

16. The gas flow indicator device of claim 1, wherein the concealment member is able to move, between a first position in which the indicator member is concealed or obscured and a second position in which the indicator member is sufficiently exposed, or fully or substantially fully exposed, over a distance enabling a clear visual indication of gas flow through the device, with the arrangement such that, when so exposed, the indicator member can readily be seen through the viewing window portion of the sidewall of the housing by a person in close proximity, such as adjacent to the device and preferably also from a considerable distance such as from five to ten metres, or further, from the device.

17. The gas flow indicator device of claim 16, wherein the viewing window portion is at least translucent, but preferably also is sufficiently transparent to facilitate viewing of the indicator member, when exposed, and most preferably is of high transparency.

18. The gas flow indicator device of claim 16, wherein the viewing window portion extends around the full circumferential extent of the sidewall of the housing adjacent to the first end, or comprises two or more regions spaced circumferentially around that wall of the housing adjacent to the first end.

19. The gas flow indicator device of claim 16, wherein the viewing window portion is of a high-transparency plastics or glass material, such as of a material also having a high level of clarity.

20. The gas flow indicator device of claim 16, wherein the material of which the remainder of the housing is made may be transparent, translucent or opaque, as required.

21. The gas flow indicator device of claim 16, wherein the housing is of unitary or integral form and made of a single material, preferable a rigid plastics material such as a suitable engineering plastics material.

22. The gas flow indicator device of claim 1, wherein the housing is circular in cross-sections perpendicular to the direction of spacing between the first and second ends, with the housing having an inner surface that is substantially cylindrical and of substantially constant circular transverse cross-section between the first and second ends, and with the sidewall also having an outer surface that is substantially cylindrical and of substantially constant circular cross-section.

23. The gas flow indicator device of claim 22, wherein the housing has an outer surface of the sidewall that departs from a cylindrical form, at least along an initial section of its longitudinal extent from adjacent to the first end, with that initial section extending around the gas flow indicator member.

24. The gas flow indicator device of claim 23, wherein the outer surface of the sidewall, over that initial section of its longitudinal extent, smoothly increases in diameter to a maximum in a direction away from the first end towards the second end, and thereafter smoothly decreases in diameter substantially to the diameter at the first end, so as to have a convex longitudinal form.

25. The gas flow indicator device of claim 1, wherein at the first end of the housing, the inlet port is defined by a spigot that projects from the first end of the housing in a direction away from the second end, and that enables connection of a gas supply conduit to the housing.

26. The gas flow indicator device of claim 25, wherein the spigot has an extension that projects into the interior of the housing to provide a hub which acts as the indicator member, or on, within or around which the gas flow indicator member is mounted, coated or otherwise provided.

27. The gas flow indicator device of claim 26, wherein in the arrangement where the indicator member is mounted on the hub, the indicator member preferably has an axial extent that is substantially the same as, or slightly greater than, the length of the hub, with the indicator member being a firm friction fit on the hub or by the indicator member being bonded or welded onto the hub, or by the indicator member having an end, adjacent to the end wall at the first end of the housing, by which the indicator member is bonded or welded to the end wall or the indicator member has, at its end remote from the first end of the housing, a flange that overlaps the corresponding end of the hub, with the flange bonded or welded to that end of the hub.

28. The gas flow indicator device of claim 25, wherein the indicator member is bonded or welded to an end wall of the housing at the first end, or mechanically engaged with that end wall such a by screw-threaded engagement or a snap fit in or around the inlet port.

29. The gas flow indicator device of claim 1, wherein the skirt of the concealment member has an outer surface that is spaced from the inner surface of the sidewall of the housing, with a spacing defined between the surfaces throughout the extent of movement of the concealment member longitudinally within the housing.

30. The gas flow indicator device of claim 29, further including guide members that maintain the concealment member in a substantially co-axial relationship with the housing, such guide members preferably comprising a plurality of circumferentially spaced projections that stand proud, or project inwardly, of the inner surface of the housing so as to be contactable with the outer surface of the skirt of the concealment member, or the converse, or a plurality of longitudinal ribs on the inner surface of the sidewall of the housing or the outer surface of the concealment member.

31. The gas flow indicator device of claim 1, wherein the inner surface of the skirt of the concealment member, when the indicator member is concealed or obscured, is spaced from the outer peripheral surface of the indicator member, thereby avoiding contact between the skirt of the concealment member and the indicator member, and thereby obviates friction that could resist movement of the concealment member relative to the indicator member, with the skirt of the concealment member and the indicator member each being of substantially uniform wall thickness along its respective axial extent and of similar or substantially the same wall thickness.

32. A gas delivery device, gas delivery system or gas supply conduit including the gas flow indicator device of claim 1.

* * * * *